(12) United States Patent
Takeuchi et al.

(10) Patent No.: US 10,660,882 B2
(45) Date of Patent: May 26, 2020

(54) PROPHYLACTIC OR THERAPEUTIC AGENT FOR GIANT CELL TUMORS OCCURRING IN BONE AND SOFT TISSUE OR FOR CHONDROSARCOMA

(71) Applicant: NIPPON CHEMIPHAR CO., LTD., Tokyo (JP)

(72) Inventors: Akihiko Takeuchi, Ishikawa (JP); Hiroyuki Tsuchiya, Ishikawa (JP)

(73) Assignee: NIPPON CHEMIPHAR CO., LTD., Tokyo (JP)

( * ) Notice: Subject to any disclaimer, the term of this patent is extended or adjusted under 35 U.S.C. 154(b) by 0 days.

(21) Appl. No.: 14/387,981

(22) PCT Filed: Mar. 18, 2013

(86) PCT No.: PCT/JP2013/057706
§ 371 (c)(1),
(2) Date: Sep. 25, 2014

(87) PCT Pub. No.: WO2013/146435
PCT Pub. Date: Oct. 3, 2013

(65) Prior Publication Data
US 2015/0045396 A1   Feb. 12, 2015

(30) Foreign Application Priority Data

Mar. 26, 2012   (JP) .................................. 2012-070351
Oct. 25, 2012   (JP) .................................. 2012-235784

(51) Int. Cl.
| | |
|---|---|
| *A61K 31/4439* | (2006.01) |
| *A61K 31/167* | (2006.01) |
| *A61K 31/192* | (2006.01) |
| *A61K 31/196* | (2006.01) |
| *A61K 31/405* | (2006.01) |
| *A61K 31/421* | (2006.01) |
| *A61K 31/427* | (2006.01) |
| *A61K 31/517* | (2006.01) |
| *A61K 31/38* | (2006.01) |
| *G01N 33/50* | (2006.01) |
| *A61K 45/06* | (2006.01) |
| *C12Q 1/6876* | (2018.01) |

(52) U.S. Cl.
CPC ........ *A61K 31/4439* (2013.01); *A61K 31/167* (2013.01); *A61K 31/192* (2013.01); *A61K 31/196* (2013.01); *A61K 31/38* (2013.01); *A61K 31/405* (2013.01); *A61K 31/421* (2013.01); *A61K 31/427* (2013.01); *A61K 31/517* (2013.01); *A61K 45/06* (2013.01); *C12Q 1/6876* (2013.01); *G01N 33/5023* (2013.01); *C12Q 2600/106* (2013.01); *C12Q 2600/158* (2013.01)

(58) Field of Classification Search
CPC .................................................. A61K 31/4439
See application file for complete search history.

(56) References Cited

U.S. PATENT DOCUMENTS

| | | | |
|---|---|---|---|
| 6,140,364 A | 10/2000 | Falck et al. | |
| 6,635,771 B2 | 10/2003 | McKew et al. | |
| 6,797,708 B2 | 9/2004 | McKew et al. | |
| 6,984,735 B2 | 1/2006 | McKew et al. | |
| 7,101,875 B2 | 9/2006 | McKew et al. | |
| 7,605,156 B2 | 10/2009 | McKew et al. | |
| 7,713,964 B2 | 5/2010 | McKew et al. | |
| 7,906,548 B2 | 3/2011 | McKew et al. | |
| 2003/0144282 A1 | 7/2003 | McKew et al. | |
| 2003/0166649 A1* | 9/2003 | McKew .............. | C07D 209/14 514/228.2 |
| 2003/0220374 A1 | 11/2003 | Needleman | |
| 2005/0209292 A1 | 9/2005 | Chuang et al. | |
| 2006/0088601 A1 | 4/2006 | Overby et al. | |
| 2006/0240014 A1 | 10/2006 | Sukhatme | |
| 2007/0232586 A1 | 10/2007 | Ohmoto et al. | |
| 2008/0279938 A1* | 11/2008 | Cho ..................... | A61K 9/2027 424/470 |
| 2009/0306074 A1 | 12/2009 | Darcy et al. | |
| 2011/0224675 A1 | 9/2011 | Tofighi et al. | |
| 2015/0297793 A1 | 10/2015 | McKay | |
| 2016/0303073 A1 | 10/2016 | Takeuchi et al. | |

FOREIGN PATENT DOCUMENTS

| | | |
|---|---|---|
| CN | 101628888 A | 1/2010 |
| EP | 2 832 367 | 2/2015 |
| JP | H06-192084 | 7/1994 |
| JP | 2004-073859 | 3/2004 |
| JP | 2005-200419 | 7/2005 |
| JP | 2005-323802 A | 11/2005 |
| JP | 2005-343802 | 12/2005 |

(Continued)

OTHER PUBLICATIONS

Takeuchi et al., *J. Jpn. Orthop. Assoc.*, vol. 86, No. 8, p. S1319, 2012.
Woo et al., "Anticancer Activity of Thymoquinone in Breast Cancer Cells: Possible Involvement of PPAR-γ Pathway", *Biochemical Pharmacology*, vol. 82, pp. 464-475, 2011.
Papi et al., "RXRγ and PPARγ Ligands in Combination to Inhibit Proliferation and Invasiveness in Colon Cancer Cells", *Cancer Letters*, vol. 297, pp. 65-74, 2010.
Takahashi et al., "Activation of PPARγ Inhibits Cell Growth and Induces Apoptosis in Human Gastric Cancer Cells", *FEBS Letters*, vol. 455, pp. 135-139, 1999.
Yamazaki et al.., "Nonsteroidal Anti-Inflammatory Drugs Induce Apoptosis in Association with Activation of Peroxisome Proliferator-Activated Receptor γ in Rheumatoid Synovial Cells", *The Journal of Pharmacology and Experimental Therapeutics*, vol. 302, No. 1, pp. 18-25, 2002.

(Continued)

*Primary Examiner* — Barbara P Badio
(74) *Attorney, Agent, or Firm* — Greenblum & Bernstein, P.L.C.

(57) ABSTRACT

The present invention provides a prophylactic or therapeutic agent for giant cell tumors occurring in a bone and soft tissue or for chondrosarcoma, which comprises a non-steroidal anti-inflammatory agent or thiazolidine derivative as an active ingredient, and the like.

9 Claims, 35 Drawing Sheets
(21 of 35 Drawing Sheet(s) Filed in Color)

(56) References Cited

FOREIGN PATENT DOCUMENTS

| | | |
|---|---|---|
| JP | 2006-501136 | 1/2006 |
| JP | 2007-015930 | 1/2007 |
| JP | 2009-533467 | 9/2009 |
| JP | 6205403 B2 | 9/2017 |
| WO | 2005/103012 | 11/2005 |
| WO | 2008/026729 | 3/2008 |
| WO | 2008/109727 | 9/2008 |
| WO | 2008/109731 | 9/2008 |
| WO | 2008/109737 | 9/2008 |
| WO | 2010/001601 | 1/2010 |
| WO | 2011/073788 | 6/2011 |
| WO | 2011/103130 | 8/2011 |
| WO | 2011/103134 | 8/2011 |
| WO | 2011/149841 | 12/2011 |
| WO | 2015/046388 | 4/2015 |

OTHER PUBLICATIONS

Kitamura et al., "Peroxisome Proliferator-activated Receptor γ Induces Growth Arrest and Differentiation Markers of Human Colon Cancer Cells", *Jpn. J. Cancer Res.*, vol. 90, pp. 75-80, 1999.
Kim et al., "Apoptotic Action of Peroxisome Proliferator-Activated Receptor-γ Activation in Human Non-Small-Cell Lung Cancer is Mediated via Proline Oxidase-Induced Reactive Oxygen Species Formation", *Molecular Pharmacology*, vol. 72, No. 3, pp. 674-685, 2007.
Nishida et al., "Inhibition of Human Chondrosarcoma Cell Growth via Apoptosis by Peroxisome Proliferator-Activated Receptor-γ", *British Journal of Cancer*, vol. 86, No. 8, pp. 1303-1309, 2002.
Li et al., "Growth Inhibition and Differentiation Induced by Peroxisome Proliferator Activated Receptor Gamma Ligand Rosiglitazone in Human Melanoma Cell Line A375", *Medical Oncology*, vol. 23, No. 3, pp. 393-402, 2006.
Vaish et al., "The Role of NF-κb and PPARγ in Experimentally Induced Colorectal Cancer and Chemoprevention by Cyclooxygenase-2 Inhibitors", *Tumor Biol.*, vol. 31, No. 5, pp. 427-436, 2010.
Xie et al., "Rosiglitazone and ATRA on Gastric Cancer SGC7901 Cell Line Proliferation In Vitro", *Journal of Chinese Physician*, vol. 12, No. 6, pp. 743-747, 2010 (including English language abstract).
International Preliminary Report on Patentability for PCT/JP2013/057706 dated Oct. 1, 2014, along with an English language translation.
International Search Report for PCT/JP2013/057706 dated May 28, 2013, along with an English language translation.
Otsuka, "Development of Endogenous Signal Responsive Implanted Drug Delivery System in Hard Tissues", *Advances in Pharmaceutical Sciences*, vol. 14, pp. 37-44, 1998.
Office Action issued in Japanese Patent Application No. 2014-507736, dated Aug. 25, 2015, along with an English language translation.
Office Action issued in New Zealand Patent Application No. 700872, dated Sep. 28, 2015.
Nishida et al., "Chondrosarcoma Peroxisome Proliferator-Activated Receptor", *PPAR Research*, vol. 274, No. 24, pp. 1-7, 2008.
De Chiara et al., "Multicentric Giant Cell Tumor with Viral-like Inclusions Associated with Paget's Disease of Bone: A Case Treated by Steroid Therapy", *Oncology Reports*, vol. 5, pp. 317-320, 1998.
Extended European Search Report issued in EP Patent Application No. 13769796.7, dated Nov. 13, 2015.
New Zealand Further Examination Report in respect to New Zealand IP No. 700872, dated Apr. 21, 2016.
New Zealand Office Action in respect to New Zealand Application No. 700872, dated Sep. 14, 2016.
New Zealand Office Action in respect to New Zealand Application No. 700872, dated Aug. 11, 2016.
Pain Clinic, 2009, 30(11), pp. 1587-1591.
Ventafridda et al., The Journal of International Medical Research, 1990, 18, 21-29.
The Journal of Practical Pharmacy, 2010, 61(10), pp. 3110-3115.
Japanese Office Action dated Mar. 21, 2017 issued in Japanese Patent Application No. 2015-252893 with machine English translation.
Takeuchi et al., "Complete Necrosis of a Giant Cell Tumor with High Expression of PPARγ: A Case Report"; Anticancer Research 33, XP055345576; May 1, 2013; pp. 2169-2174.
Takeuchi et al., "Activation of peroxisome proliferator-activated receptor gamma is a novel therapeutic means for giant cell tumor P4:103"; Abstracts 26th European Musculoskeletal Oncology Society meeting, XP055345586; May 1, 2013; pp. 1.
Extended European Search Report issued in Patent Application No. 14847606.2, dated Feb. 23, 2017.
Australian Office Action issued in Australian Patent Appl. No. 2013238126, dated Dec. 21, 2016.
The Journal of the Japanese Orthopedic Association, 2013, 87(8): 1-8-22.
2013 AAOS (American Association of Orthopedic Surgeons) Annual Meeting Abstract Paper 341.
26th Eur. Musculoskeletal Oncology Society Meeting 2013, Abstract P4: 103.
The Journal of the Japanese Orthopedic Association, 2013; 87(6): 1-2-FP3-8.
ISOLS 2013 Abstract No. 205 (Annual Meeting of International Society of Limb Salvage 2013, Abstract No. 310).
Anticancer Research, 2013; 33, pp. 2169-2174.
The Journal of the Japanese Orthopedic Association, 2013; 87(8): 1-8-20.
ISOLS 2013 Abstract No. 205 (Annual Meeting of International Society of Limb Salvage 2013, Abstract No. 205).
Naruse T. et al., Carcinogenesis, 2006, vol. 27, No. 3, pp. 584-592.
Lee E. J. et al., Exp Mol Med, 2007, vol. 39, No. 4, pp. 469-476.
Lili Fu et al., Chemotherapy, 2009, vol. 55, No. 6, pp. 468-476.
Long H. et al., Chinese Journal of Bone and Joint, 2012, vol. 1, No. 2, pp. 136-140.
Aizawa, The Journal of the Japanese Orthopedic Association, 2009, vol. 83, No. 8, pp. S1259.
Shen Z. N. et al., Biochem Biophys Res Commun, 2005, vol. 328, No. 2, pp. 375-382.
International Search Report and Written Opinion issued in PCT/JP2014/075542 with English Translation, dated Dec. 16, 2014.
International Preliminary Report on Patentability issued in PCT/JP2014/075542 with English Translation, dated Mar. 29, 2016.
Japanese Notification of Reasons for Refusal with English Translation in respect to Japanese Appl. No. 2015-252893, dated Nov. 1, 2016.
English Abstract of Japanese Reference 2006/501136.
English Abstract of Japanese Reference 2005-200419.
English Abstract of Japanese Reference 2009-533467.
European Office Action from Application No. 14847606.2 dated Feb. 13, 2018.
Australian Examination Report No. 2 in respect to Australian Application No. 2013238126, dated Aug. 31, 2017.
European Office Action in respect to European Application No. 13769796.7, dated Sep. 15, 2017.
Wassef et al (Journal of Biomedical Materials Research, Part B: Applied Biomaterials, 2008, vol. 86B, pp. 63-73) (Year: 2008).
Grommes et al. (Molecular Pharmacology, 2006, vol. 70, pp. 1524-1533) (Year: 2006).
The abstract of Langova et al (Australian Veterinary Practitioner, 2004, vol. 34, pp. 98-102) (Year: 2004.
Wurthwein et al (European Journal of Clinical Pharmacology, 2005,vol. 60, pp. 883-888) (Year: 2005).
Tsai et al. ( The Lancet Oncology, 2005, vol. 6, pp. 997-999)(Year: 2005).
Kasper et al (International Journal of Clinical Oncology, 2005, vol. 10, pp. 438-440) (Year:2005).
The abstract of Yan (CN 1458158, 20031126( (Year: 2003).
Sardone et al. (Diabetes, 2011, vol. 60, pp. 3271-3278) (Year: 2011).
Jones et al.; Circulation, 2009:119:3125-3132, Jun. 8, 2009, with data supplemental; as (Arthritis and Rheumatism, 2010, vol. 62, pp. 2726-2735) (Year: 2010).
Hirabayashi et al (Journal of Controlled Release, 2001, vol. 79, pp. 183-191) (Year: 2001).

(56) References Cited

OTHER PUBLICATIONS

Cheng et al (Calcified Tissue International, 2004, vol. 75, pp. 71-77) (Year: 2004).
Office Action dated Mar. 22, 2018 in U.S. Appl. No. 15/023,896.
Japanese Office Action (and English Translation) issued with respect to Application No. 2015-539360, dated Jul. 3, 2018.
Bernardo et al., "Nuclear receptor peroxisome proliferator-activated receptor-y is activated in rat microglial cells by the anti-inflammatory drug HCT1026, a derivative of flurbiprofen", Journal of Neurochemistry, 2005, 92, pp. 895-903.
Zou et al., "PPARy agonists inhibit TGF-B-PKA signaling in glomerulosclerosis", Acta Pharmacologica Sinica, 2010, 31, pp. 43-50.
Maeyama et al., "Nuclear Receptors as Targets for Drug Development: Peroxisome Proliferator-Activated Receptor y in Mast Cells: Its Roles in Proliferation and Differentiation", Journal of Pharmacological Sciences, 97, pp. 190-194, 2005.
Dufresne et al., "Giant-cell tumor of bone, anti-RANKL therapy", BoneKEy Reports 1, Article No. 149, pp. 1-8, 2012.
European Office Action issued in European patent application No. 14847606.2, dated Oct. 15, 2018.
Matsumoto et al., "NSAID zaltoprofen possesses novel antinociceptive mechanism through blockage of B2-type bradykinin receptor in nerve endings", Neuroscience Letters, 2006, vol. 397, No. 3, p. 249-253, XP55508938.
Japanese Office Action issued in Japanese patent application No. 2015-539360, dated Nov. 6, 2018, with English machine translation.
Diaz-Rodriguez et al., "Effect of acetaminophen (paracetamol) on human osteosarcoma cell line MG63", Acta Pharmacol Sin, 2010, vol. 31, No. 11, p. 1495-1499.
E. De Luna-Bertos et al., "Effect of Aspirin on Cell Growth of Human MG-63 Osteosarcoma Line", ScientificWorldJournal, 2012, Article ID 834246, including pp. 1-6.
Diaz-Rodriguez et al., "Effects of Indomethacin, Nimesulide, and Diclofenac on Human Mg-63 Osteosarcoma Cell Line", Bio Res Nurs, 2012, vol. 14, No. 1, p. 98-107.
Canadian Office Action issued with respect to Canadian Application No. 2,868,311, dated Dec. 19, 2018.
Final Office Action issued with respect to U.S. Appl. No. 15/023,896, dated Dec. 13, 2018.
First Office Action dated Sep. 4, 2018 issued in the corresponding Chinese Patent Application No. 201610647601 with its English machine translation.
Second Office Action dated May 8, 2019 issued in the corresponding Chinese Patent Application No. 201610647601.
World Pharmacy, 1995, pp. 306-307.
Ming H. Zheng, "Gene Expression of Vascular Endothcial Growth Factor in Giant Cell Tumors of Bone", Human Pathology, pp. 804-812, Jul. 2000.
Chin J Pancreatol, Oct. 2007, vol. 7, No. 5, pp. 313-316, English Abstract.
First Office Action dated Jan. 27, 2016 issued in the corresponding Chinese Patent Application No. 201380016296 with its English machine translation.
Second Office Action dated Dec. 14, 2016 issued in the corresponding Chinese Patent Application No. 201380016296 with its English machine translation.
Third Office Action dated Sep. 5, 2017 issued in the corresponding Chinese Patent Applicaiton No. 201380016296 with its English machine translation.
Office Action dated Jun. 27, 2019 in U.S. Appl. No. 15/023,896.
Liu et al., Chinese Medical Journal, 2012, vol. 125, pp. 3719-3724.
Stangler et al., Journal of International Medical Research, 2000, vol. 28, pp. 149-167.
Office Action dated Jan. 6, 2020 issued in Chinese Application No. 201610647601.0 with English translation.
Handbook of Orthopaedic Resident, editor-in-chief: LIU Shiqing, pp. 505-506, Jan. 31, 2005, discussed in English Translation of Chinese Office Action.
Contemporary Multimedia Atlas of Needle Aspiration Cytology Diagnostics, editor-in-chief: Wang Yongcai Tianjin Science & Technology Press, p. 385, Jul. 31, 2004, discussed in English translation of Chinese Office Action.
English translation of Second Office Action dated May 8, 2019 issued in the corresponding Chinese Patent Application No. 201610647601.
Chinese Examiner's Summary; Excerpts from 2nd Chinese Official Action, dated May 8, 2019, in Chinese Patent Application No. 201610647601 pertaining to World Pharmacy, 1995, pp. 306-307.
Paknesban et al., Investigative Ophthalmology & Visual Science, Sep. 2008, vol. 49, No. 9, pp. 3909-3913.
Office Action dated Sep. 19, 2019 issued in Canadian Application No. 2,868,311.
Potter, Am. Fam. Physician, 72(3), 436-437, Aug. 1, 2005.
Office Action dated Jul. 29, 2019 (with English translation) issued in Korean patent application No. 10-2014-7029881.
Extended European Search Report dated Feb. 28, 2020 issued in European Patent Application No. 19210770.4.
Korean Office Action dated Feb. 28, 2020 issued in Korean Patent Application No. 10-2014-7029881, with English translation.
Balke Maurice et al: BMC Cancer Biomed Central, London GB, vol. 10, No. 1, Aug. 29, 2010 (Aug. 29, 2010), p. 462, 8 pages.
Hamid Namazi: Annals of Surgical Oncology, Springer-Verlag, NE, vol. 15, No. 8, Jan. 23, 2008 (Jan. 23, 2008), pp. 2350-2351.
Arne Streitbuger et al: International Orthopedics, Springer, Berin, DE, vol. 35, No. 9, Oct. 2, 2010 (Oct. 2, 2010), pp. 1369-1373.
Lyles et al. Journal of Bone and Mineral Research, vol. 16, No. 8, pp. 1379-1387 (2001).

\* cited by examiner

PVNS (diffuse-type GCT)

Nodular tenosynovitis (GCT of tendon sheath)

PROPHYLACTIC OR THERAPEUTIC AGENT FOR GIANT CELL TUMORS OCCURRING IN BONE AND SOFT TISSUE OR FOR CHONDROSARCOMA

TECHNICAL FIELD

The present invention relates to a prophylactic or therapeutic agent and the like for giant cell tumors occurring in a bone and soft tissue or for chondrosarcoma, in which agent a non-steroidal anti-inflammatory agent or a thiazolidine derivative is used. The present invention also relates to a screening method for selecting a substance as a prophylactic or therapeutic agent for giant cell tumors occurring in a bone and soft tissue or for chondrosarcoma, which substance induces expression of PPARγ, and thereby induces apoptosis or fat cell differentiation.

BACKGROUND ART

As giant cell tumors occurring in a bone and soft tissue, there are known osteoclastoma occurring in a bone (giant cell tumor of bone), giant cell tumor of tendon sheath occurring in a soft tissue, pigmented villonodular synovitis, and the like.

Osteoclastoma is a benign tumor frequently occurring in circumferences of the knee joints of young to middle- or advanced-aged persons, and the patients' man-and-woman ratio is 1:1.3 to 1.5, which means higher morbidity of women. Osteoclastoma accounts for about 5% of the total bone tumors, and accounts for about 20% of benign bone tumors. Although it is a benign tumor, the recurrence rate thereof is as high as 10 to 30%, and therapeutic treatment may sometimes be troubled by metastases to lung or malignant transformation. The major pathological finding is hyperplasia of multinucleated giant cells and monocyte cells, and spindle cells are observed among them. It is considered that the body of the tumor is not these multinucleated giant cells, but fibroblast-like spindle cells present in the stroma. Further, since it occurs in the vicinity of a joint such as knee joint, shoulder joint, and wrist joint, it is important how the recurrence is prevented, and how a treatment is performed with conserving the joint function.

Giant cell tumor of tendon sheath is a neoplastic disease occurring from tendon sheath, joint, or synovial membrane of synovial bursa. It is classified into the localized type and diffused type on the basis of the growth type of a lesion, and it is generally considered that a lesion of the localized type is synonymous to the giant cell tumor of tendon sheath, and giant cell tumor of tendon sheath of the diffused type is synonymous to the pigmented villonodular synovitis. Giant cell tumor of tendon sheath frequently occurs in women in their thirties to fifties, and in about 85% of patients, it occurs in the vicinity of joints of fingers or on the flexor tendon, and it secondly frequently occurs in toes. It may sometimes infiltrate into bones. As the major pathological findings, there are mainly orbicular-ovate to spindle-shaped histiocyte-like monocytes, and multinucleated giant cells and foam cells are accompanied by hemosiderosis. As the therapeutic treatment, tumor resection (simple enucleation) is performed as in the case of benign tumors, but the recurrence rate is reported to be 4 to 30%.

Pigmented villonodular synovitis occurs in relatively young adults not older than 40, and slightly more frequently occurs in women. It most frequently occurs in the knee joint, and also occurs in the hip, leg, elbow, shoulder joints, and the like. Villus images and tubercle-like proliferation of the synovial membrane are caused in the joints, and hemarthrosis is often observed. Since it may infiltrate into bones, secondary osteoarthritis may occur. As the pathological findings, there are intermingled synovial cell-like monocytes, multinucleated giant cells, foam cells, siderophores, inflammatory cells, and the like. As the therapeutic treatment, the tumor is surgically resected, but total resection is difficult, and therefore the recurrence rate is as high as 40 to 50%.

For all of osteoclastoma, giant cell tumor of tendon sheath, and pigmented villonodular synovitis, any effective therapies have not been developed at present, except for surgical operation.

Chondrosarcoma accounts for about 20% of primary malignant bone tumors, and shows the secondly highest occurrence frequency following that of bone sarcoma. It is histologically classified into conventional chondrosarcoma, periosteal chondrosarcoma, mesenchymal chondrosarcoma, dedifferentiated chondrosarcoma, clear-cell chondrosarcoma, extraskeletal myxoid chondrosarcoma, and the like. Typical chondrosarcoma frequently occurs in thirties to fifties, and slightly more frequently occurs in men. It most frequently occurs in the pelvic bone, and secondly frequently occurs in rib, proximal femur, proximal humerus, and distal femur. Mesenchymal chondrosarcoma frequently occurs in persons from between the age of ten and nineteen to those in thirties, who are younger than those favorite for conventional chondrosarcoma, and frequently occurs in jaw, spine, iliac bone, rib, distal part of femur, and the like. Dedifferentiated chondrosarcoma is a non-cartilaginous highly malignant tumor developed from a low malignancy conventional chondrosarcoma, and they are developed in contiguity with each other, but with a definite boundary. It occurs in persons in their fifties or sixties, and most frequently occurs in femur, and secondly frequently occurs in pelvis and humerus. Clear-cell chondrosarcoma frequently occurs in persons in their twenties to fifties, and in about ⅔ of the patients, it occurs in humeral head or femoral head. It also occurs in cranical bone, spine, and bones of hand and foot. Extraskeletal myxoid chondrosarcoma frequently occurs in persons in their forties and fifties, and may occur in deep part soft tissues of proximal parts of extremities such as thigh, and of the truncus, and soft tissues such as end parts of extremities, mediastinum and retroperitoneum. For these types of chondrosarcoma, any effective therapies have not been developed so far, except for surgical operation.

The peroxisome proliferator-activated receptor γ (PPARγ) is a protein belonging to the intranuclear receptor superfamily, and also functions as a transcription factor. Although PPARγ is mainly distributed over fat tissues, and participates in fat cell differentiation and the like, expression thereof is also observed in macrophages, vascular endothelial cells and the like. As the other activities thereof, it has been reported that the protein has an antidiabetic activity, anti-arteriosclerotic activity, bone metabolism related activity, antitumor activity, and anti-inflammatory activity. For example, it has been reported that activation of PPARγ induces apoptosis in various tumors (Non-patent documents 1 and 2), and expression of PPARγ has been confirmed in various cancer cells, such as cells of breast cancer (Non-patent document 3), colon cancer (Non-patent document 4), or lung cancer (Non-patent document 5). Moreover, it has been reported that activation of PPARγ is also induced by a non-steroidal anti-inflammatory agent besides a PPARγ ligand, resulting induction of cell death (Non-patent document 6).

However, neither expression of PPARγ in giant cell tumor occurring in a bone and soft tissue nor treatment targeting PPARγ have been reported so far. There has only been disclosed for an anti-inflammatory activity and suppression of cell proliferation of giant cell tumor of tendon sheath and pigmented villonodular synovitis which is a disease analogous to osteoclastoma, by suppression of IL-6 production (Patent document 1).

PRIOR ART REFERENCES

Patent Document

Patent document 1: WO2008/026729

Non-Patent Documents

Non-patent document 1: Jpn. J. Cancer Res., 1999, 90:75-80
Non-patent document 2: FEBS Lett., 1999, 455:135-139
Non-patent document 3: Biochem. Pharmacol., 2011, 82:464-475
Non-patent document 4: Cancer Lett., 2010, 297:65-74
Non-patent document 5: Mol. Pharmacol., 2007, 72:674-685
Non-patent document 6: J. Pharmacol. Exp. Ther., 2002, 302:18-25

SUMMARY OF THE INVENTION

Object to be Achieved by the Invention

An object of the present invention is to provide a substance that induces expression of PPARγ in giant cell tumor occurring in a bone and soft tissue or that in chondrosarcoma, and induces apoptosis or fat cell differentiation mediated by PPARγ as a prophylactic or therapeutic agent for giant cell tumors occurring in a bone and soft tissue or for chondrosarcoma. Another object of the present invention is to provide a screening method for selecting a substance as a prophylactic or therapeutic agent for giant cell tumors occurring in a bone and soft tissue or for chondrosarcoma, which substance induces expression of PPARγ, and thereby induces apoptosis or fat cell differentiation.

Means for Achieving the Object

The inventors of the present invention observed that PPARγ was not usually expressed in giant cell tumor occurring in a bone and soft tissue or chondrosarcoma. Whilst they also observed that PPARγ was expressed in osteoclastoma, which is giant cell tumor occurring in a bone and soft tissue, in a patient administered with zaltoprofen which is one of non-steroidal anti-inflammatory agents and has a PPARγ-agonistic activity, and that apoptosis or differentiation into fat cells were induced. The inventors of the present invention further conducted researches on the basis of the aforementioned findings, and as a result, accomplished the present invention.

The present invention thus provides the followings:
[1] A prophylactic or therapeutic agent for giant cell tumors occurring in a bone and soft tissue or for chondrosarcoma, which comprises a non-steroidal anti-inflammatory agent or a thiazolidine derivative as an active ingredient;
[2] The prophylactic or therapeutic agent according to [1] mentioned above, wherein the non-steroidal anti-inflammatory agent is selected from the group consisting of zaltoprofen, diclofenac, indomethacin, oxaprozin, acetaminophen, and ketoprofen;
[3] The prophylactic or therapeutic agent according to [1] mentioned above, wherein the thiazolidine derivative is selected from the group consisting of troglitazone, rosiglitazone, pioglitazone, baraglitazone, and rivoglitazone;
[4] The prophylactic or therapeutic agent according to any one of [1] to [3] mentioned above, wherein the giant cell tumor occurring in a bone and soft tissue is selected from the group consisting of osteoclastoma, giant cell tumor of tendon sheath, and pigmented villonodular synovitis;
[5] A method of screening a prophylactic or therapeutic agent for giant cell tumors occurring in a bone and soft tissue or for chondrosarcoma, which comprises the following steps:
(1) the step of culturing a cell derived from giant cell tumors occurring in a bone and soft tissue or chondrosarcoma under conditions of presence and absence of a test substance,
(2) the step of measuring expression of PPARγ gene, and also measuring
(i) expression of an apoptosis-related gene, or
(ii) expression of a fat cell differentiation-related gene, under both of the conditions, and
(3) the step of selecting a test substance that significantly changes expression of the PPARγ gene, and also significantly changes
(i) expression of an apoptosis-related gene, or
(ii) expression of a fat cell differentiation-related gene, compared with those observed under the condition of absence of the test substance;
[6] The screening method according to [5] mentioned above, wherein the giant cell tumor occurring in a bone and soft tissue is selected from the group consisting of osteoclastoma, giant cell tumor of tendon sheath, and pigmented villonodular synovitis;
[7] A method for prophylactic or therapeutic treatment of giant cell tumors occurring in a bone and soft tissue or of chondrosarcoma, which comprises administering an effective amount of a non-steroidal anti-inflammatory agent or a thiazolidine derivative to a subject;
[8] The method for prophylactic or therapeutic treatment according to [7] mentioned above, wherein the non-steroidal anti-inflammatory agent is selected from the group consisting of zaltoprofen, diclofenac, indomethacin, oxaprozin, acetaminophen, and ketoprofen;
[9] The method for prophylactic or therapeutic treatment according to [7] mentioned above, wherein the thiazolidine derivative is selected from the group consisting of troglitazone, rosiglitazone, pioglitazone, baraglitazone, and rivoglitazone;
[10] The method for prophylactic or therapeutic treatment according to any one of [7] to [9] mentioned above, wherein the giant cell tumor occurring in a bone and soft tissue is selected from the group consisting of osteoclastoma, giant cell tumor of tendon sheath, and pigmented villonodular synovitis;
[11] A non-steroidal anti-inflammatory agent or a thiazolidine derivative for use in prophylactic or therapeutic treatment of giant cell tumors occurring in a bone and soft tissue or of chondrosarcoma;
[12] The non-steroidal anti-inflammatory agent or thiazolidine derivative according to [11] mentioned above, wherein the non-steroidal anti-inflammatory agent is selected from the group consisting of zaltoprofen, diclofenac, indomethacin, oxaprozin, acetaminophen, and ketoprofen;
[13] The non-steroidal anti-inflammatory agent or thiazolidine derivative according to [11] mentioned above, wherein the thiazolidine derivative is selected from the group consisting of troglitazone, rosiglitazone, pioglitazone, baraglitazone, and rivoglitazone;

[14] The non-steroidal anti-inflammatory agent or thiazolidine derivative according to any one of [11] to [13] mentioned above, wherein the giant cell tumor occurring in a bone and soft tissue is selected from the group consisting of osteoclastoma, giant cell tumor of tendon sheath, and pigmented villonodular synovitis; and the like.

Effect of the Invention

The prophylactic or therapeutic agent of the present invention can be administered to a patient with giant cell tumor occurring in a bone and soft tissue or with chondrosarcoma as a chemotherapeutic drug to be administered before or after a surgical operation, or it can be administered to a person having a risk of onset of giant cell tumor occurring in a bone and soft tissue or that of chondrosarcoma as a prophylactic agent. Further, according to the present invention, by selecting a test substance that controls PPARγ and apoptosis or fat cell differentiation, it becomes possible to retrieve a novel prophylactic or therapeutic agent for giant cell tumors occurring in a bone and soft tissue or for chondrosarcoma.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

MODES FOR CARRYING OUT THE INVENTION

Figure 1:
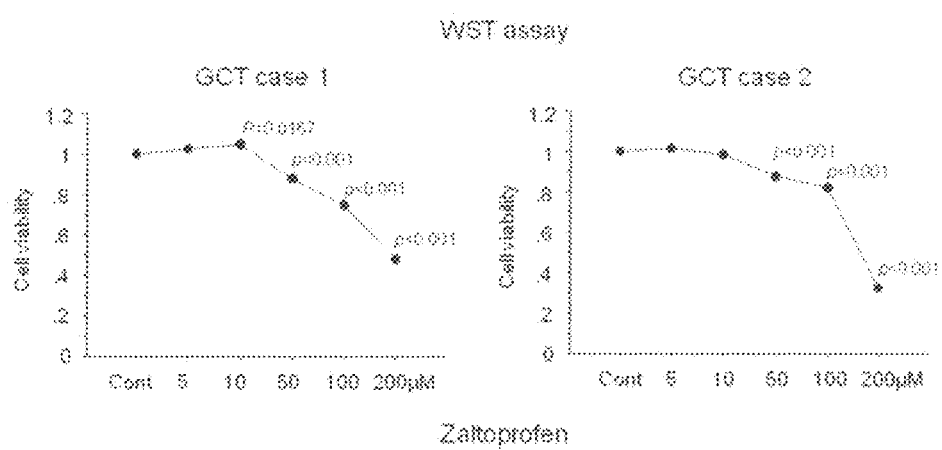
FIG. 1 Graphs showing results of suppression of proliferation of GCT cultured cells that were cultured in a zaltoprofen-containing medium.
Figure 2:
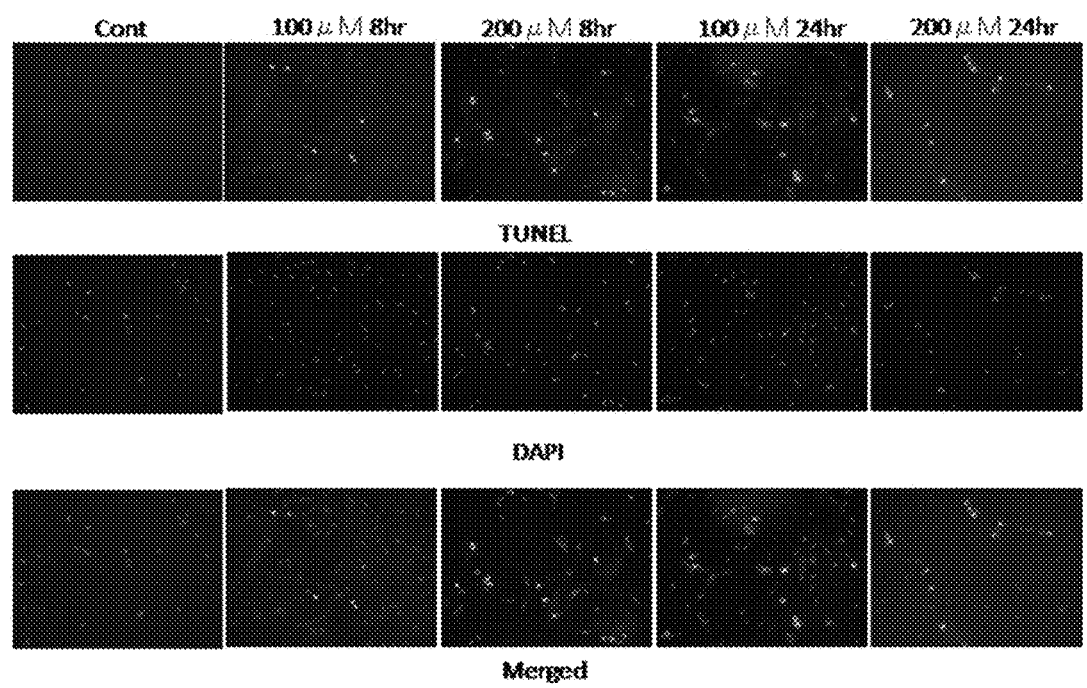
FIG. 2 Photographs showing results of Tunel assay performed with GCT cultured cells that were cultured in a zaltoprofen-containing medium.
Figure 3:
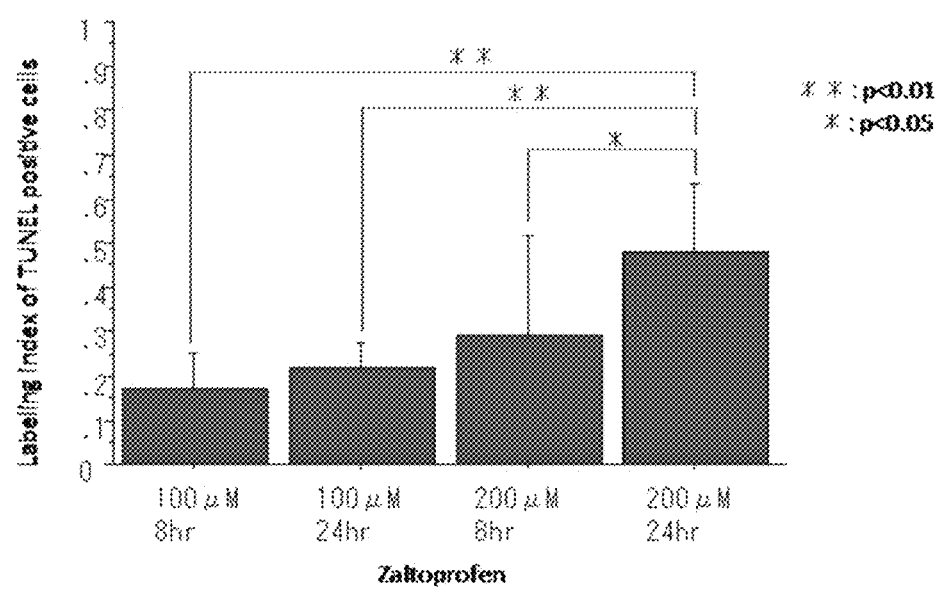
FIG. 3 A graph showing ratios of Tunel-positive cells in GCT cultured cells that were cultured in a zaltoprofen-containing medium.
Figure 4:
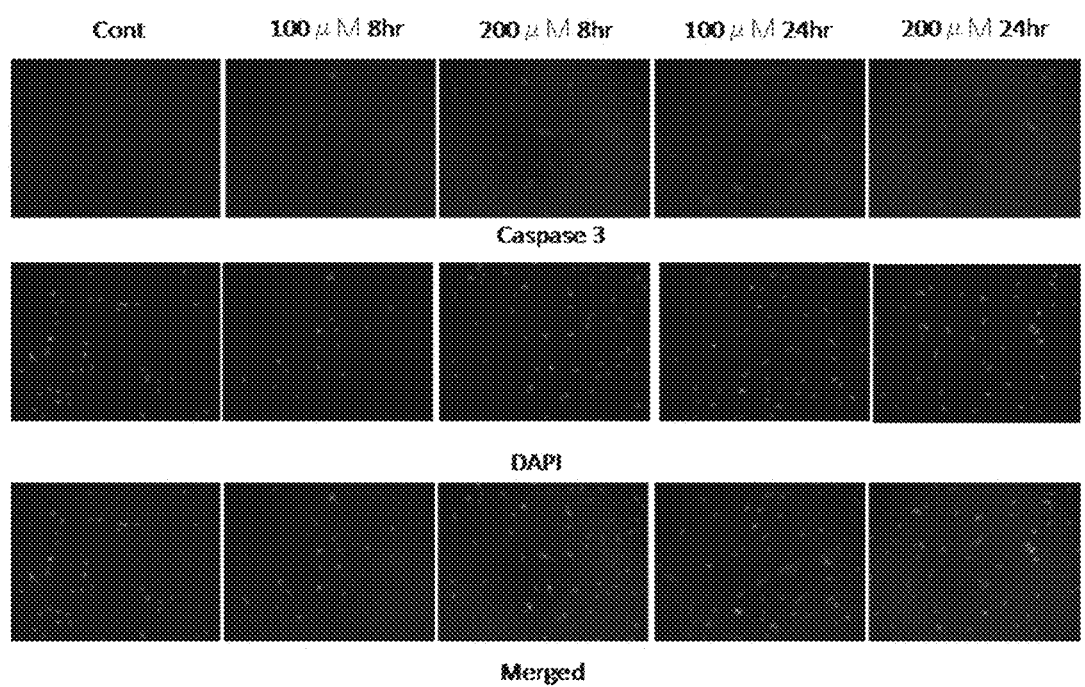
FIG. 4 Photographs showing results of caspase 3 staining of GCT cultured cells that were cultured in a zaltoprofen-containing medium.
Figure 5:
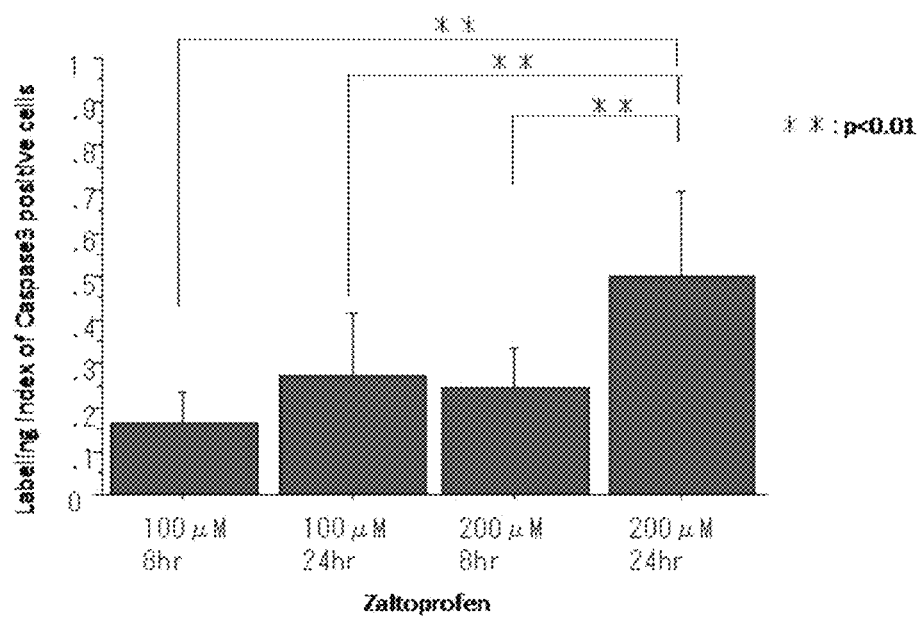
FIG. 5 A graph showing ratios of caspase 3-positive cells in GCT cultured cell cultured in a zaltoprofen-containing medium.

The inventors of the present invention found that PPARγ was not expressed in cells derived from patients with giant cell tumor occurring in a bone and soft tissue, and they also found that a specific substance having a PPARγ-agonistic activity induced expression of PPARγ in giant cell tumor occurring in a bone and soft tissue, and simultaneously induced apoptosis or fat cell differentiation. Therefore, the present invention provides a prophylactic or therapeutic agent for giant cell tumors occurring in a bone and soft tissue, which can induce apoptosis or fat cell differentiation mediated by PPARγ in giant cell tumor occurring in a bone and soft tissue on the basis of the PPARγ expression-inducing activity and the PPARγ-agonistic activity. The present invention also provides a prophylactic or therapeutic agent for chondrosarcoma, which can induce apoptosis or fat cell differentiation mediated by PPARγ on the basis of the PPARγ expression-inducing activity and the PPARγ-agonistic activity.

The giant cell tumor occurring in a bone and soft tissue to which the prophylactic or therapeutic agent of the present invention can be applied is not particularly limited, so far as giant cells developed in a bone and soft tissue are observed in the tumor. In particular, the agent of the present invention can be preferably applied to a tumor that generates giant cells in circumferences of bone, joint, or tendon sheath. The tumor in which giant cells developed in a bone and soft tissue are observed is preferably a benign tumor. Examples of such a tumor include, for example, osteoclastoma, giant cell tumor of tendon sheath, pigmented villonodular synovitis, and the like. Examples of benign giant cell tumor occurring in a bone and soft tissue also include chondroblastoma, nonossifying fibroma, osteoblastoma, aneurysmal bone cyst, and the like.

Examples of the chondrosarcoma to which the prophylactic or therapeutic agent of the present invention can be applied include conventional chondrosarcoma, periosteal chondrosarcoma, mesenchymal chondrosarcoma, dedifferentiated chondrosarcoma, clear-cell chondrosarcoma, extraskeletal myxoid chondrosarcoma, and the like.

The prophylactic or therapeutic agent of the present invention can also be used for a tumor in which expression of PPARγ is observed. Examples of such a tumor in which expression of PPARγ is observed include breast cancer, colon cancer, lung cancer, thyroid gland cancer, esophageal cancer, gastric cancer, pancreatic cancer, liver cancer, kidney cancer, vesical cancer, ovarian cancer, uterine cervix carcinoma, prostate cancer, malignant melanoma, leukemia, malignant lymphoma, liposarcoma, leiomyosarcoma, bone sarcoma, and the like.

PPARγ is a protein belonging to the intranuclear receptor superfamily, and it recognizes the PPAR response element (PPRE) when it has formed a heterodimer with the retinoid X receptor (RXR), which is one of the intranuclear receptors, and activates transcription of a gene downstream therefrom.

In the present invention, examples of such a substance having a PPARγ expression-inducing activity and a PPARγ-agonistic activity include non-steroidal anti-inflammatory agents. Therefore, the prophylactic or therapeutic agent for giant cell tumors occurring in a bone and soft tissue or chondrosarcoma that can induce apoptosis or fat cell differentiation mediated by PPARγ in giant cell tumors occurring in a bone and soft tissue or in chondrosarcoma on the basis of a PPARγ expression-inducing activity and a PPARγ-agonistic activity is, according to an embodiment of the present invention, a prophylactic or therapeutic agent for giant cell tumors occurring in a bone and soft tissue or for chondrosarcoma, which comprises a non-steroidal anti-inflammatory agent as an active ingredient. The non-steroidal anti-inflammatory agent referred herein is not particularly limited so long as it is a compound that inhibits the synthesis of prostaglandins and thromboxanes by inhibition of cyclooxygenase, and thereby exhibits an anti-inflammatory activity. Examples include, for example, zaltoprofen, diclofenac, indometacin, oxaprozin, acetaminophen, ketoprofen, and the like, and preferred examples include zaltoprofen, diclofenac, and indometacin. Other than the non-steroidal anti-inflammatory agents, examples of the substance include, for example, thiazolidine derivatives. Therefore, the prophylactic or therapeutic agent for giant cell tumors occurring in a bone and soft tissue or for chondrosarcoma that can induce apoptosis or fat cell differentiation mediated by PPARγ in giant cell tumors occurring in a bone and soft tissue or in chondrosarcoma on the basis of a PPARγ expression-inducing activity and a PPARγ-agonistic activity may also be a prophylactic or therapeutic agent for giant cell tumors occurring in a bone and soft tissue or for chondrosarcoma, which comprises a thiazolidine derivative as an active ingredient. Thiazolidine derivatives are known to activate PPARγ, and are PPARγ agonists that promote transcription of the adiponectin gene. Examples of such thiazolidine derivatives include, for example, troglitazone, rosiglitazone, pioglitazone, balaglitazone, rivoglitazone, and the like.

In the present invention, the PPARγ expression-inducing activity of the substances having a PPARγ expression-inducing activity and a PPARγ-agonistic activity, which substances include non-steroidal anti-inflammatory agents and thiazolidine derivatives, can be confirmed by the known methods described later. For example, expression thereof can be confirmed by a method of extracting mRNA from giant cell tumors occurring in a bone and soft tissue or from chondrosarcoma by an ordinary method, and performing a reverse transcription reaction and PCR using primers that enables amplification of a PPARγ transcription product, or a method of fixing giant cell tumors occurring in a bone and soft tissue or fixing chondrosarcoma, or extracting a cell disruption product, and confirming expression of a PPARγ translation product by using an antigen-antibody reaction using antibodies directed to the PPARγ translation product. The transcription product and translation product of PPARγ are known. For example, as for the transcription product, nucleotide sequence information is disclosed as GenBank accession No. BC006811, and as for the translation product thereof, amino acid sequence information is disclosed as GenBank accession No. AAH06811. Further, the PPARγ-agonistic activity can be confirmed by, for example, measuring expression level of a downstream gene, or expression level of a lipid. Examples of the gene locating downstream of PPARγ include, for example, an apoptosis-related gene, fat cell differentiation-related gene, arteriosclerosis-related gene, anti-inflammation-related gene, and the like. The apoptosis-related gene may be a gene responsible for an apoptosis signal, or may be a marker gene for apoptosis. Examples of the apoptosis-related gene include, for example, those of caspase 3, p53, and the like. As for the transcription product of caspase 3, nucleotide sequence information is disclosed as GenBank accession No. BC016926, and as for the translation product thereof, amino acid sequence information is disclosed as GenBank accession No. AAH16926. As for the transcription product of p53, nucleotide sequence information is disclosed as GenBank accession No. NM_000546, and as for the translation product thereof, amino acid sequence information is disclosed as GenBank accession No. NP_000537. The fat cell differentiation-related gene may be a gene that induces differentiation into fat cells, or may be a marker gene for fat cell differentiation. Examples of the fat cell differentiation-related gene include, for example, those of Setd8 (SET domain containing (lysine methyltransferase) 8), Setdb1 (SET domain, bifurcated 1), LPL (Lipoprotein Lipase), leptin, FABP4/aP2 (fatty acid-binding protein-4), adiponectin, a2Col6 (α chain 2 of type 6 collagen), and the like. As for the transcription product of Setd8, nucleotide sequence information is disclosed as GenBank accession No. NM_020382, and as for the translation product thereof, amino acid sequence information is disclosed as GenBank accession No. NP_065115. As for the transcription product of Setdb1, nucleotide sequence information is disclosed as GenBank accession No. BC028671, and as for the translation product thereof, amino acid sequence information is disclosed as GenBank accession No. AAH28671. As for the transcription product of LPL, nucleotide sequence information is disclosed as GenBank accession No. BC011353, and as for the translation product thereof, amino acid sequence information is disclosed as GenBank accession No. AAH11353. As for the transcription product of leptin, nucleotide sequence information is disclosed as GenBank accession No. BC069452, and as for the translation product thereof, amino acid sequence information is disclosed as GenBank accession No. AAH69452. As for the transcription product of FABP4/aP2, nucleotide sequence information is disclosed as GenBank accession No. BC003672, and as for the translation product thereof, amino acid sequence information is disclosed as GenBank accession No. AAH03672. As for the transcription product of adiponectin, nucleotide sequence information is disclosed as GenBank accession No. BC096308, and as for the translation product thereof, amino acid sequence information is disclosed as GenBank accession No. AAH96308. As for the transcription product of a2Col6, nucleotide sequence information is disclosed as GenBank accession No. BC002483, and as for the translation product thereof, amino acid sequence information is disclosed as GenBank accession No. AAH002483. Examples of the arteriosclerosis-related gene include, for example, those of AT1R (angiotensin II receptor 1), and the like. As for the transcription product of AT1R, nucleotide sequence information is disclosed as GenBank accession No. BC068494, and as for the translation product thereof, amino acid sequence information is disclosed as GenBank accession No. AAH68494. Examples of the anti-inflammation-related gene include, for example, those of NF-κB (nuclear factor kappa-light-chain-enhancer of activated B cells), and the like. As for the transcription product of NF-κB, nucleotide sequence information is disclosed as GenBank accession No. NM_003998, and as for the translation product thereof, amino acid sequence information is disclosed as GenBank accession No. NP_003989. The lipid is not particularly limited so long as it is a lipid contained in fat cells or tissues, and examples include phospholipids, glycolipids, lipoproteins, acylglycerols, ceramides, and the like.

Specifically, the PPARγ expression-inducing activity can be examined by preparing an RNA (for example, total RNA, or mRNA) fraction from a cell, and detecting the transcription product of the PPARγ gene contained in the fraction. Such an RNA fraction can be prepared by a known method such as the guanidine-CsCl ultracentrifugation method and the AGPC method, and total RNA of high purity can be quickly and conveniently prepared from a small number of cells by using a commercial kit for RNA extraction (for example, RNeasy Mini Kit produced by QIAGEN and the like). Examples of the means for detecting a transcription product of a gene in an RNA fraction include, for example, a method of using hybridization (Northern blotting, dot blotting, DNA chip analysis, and the like), a method of using PCR (RT-PCR, competitive PCR, real-time PCR, and the like), and the like. The quantitative PCR method as competitive PCR and real-time PCR is preferred, since it enables quick and convenient detection of change of expression of a gene from an extremely small amount of sample with good quantification ability.

When Northern blotting or dot blot hybridization is used, the PPARγ gene can be detected by, for example, using a nucleic acid probe that enables specific detection of a transcription product of the gene. The nucleic acid probe used for measurement of the PPARγ expression-inducing activity is a polynucleotide comprising a contiguous part or all of the gene containing about 15 or more nucleotides, preferably about 18 to 500 nucleotides, more preferably about 18 to 200 nucleotides, still more preferably about 18 to 50 nucleotides, or a polynucleotide comprising a complementary sequence thereof. Examples of the part or all of PPARγ gene include a part or all of the known nucleotide sequence of PPARγ mentioned above. The polynucleotide may be either DNA or RNA, or may be a DNA/RNA chimera. Preferably the polynucleotide includes DNA. Further, the polynucleotide used as the probe may be a double-stranded or single-stranded polynucleotide. The double-stranded polynucleotide may be a double-stranded DNA, double-stranded RNA, or a hybrid of DNA and RNA. In the case of the single-stranded polynucleotide, an antisense strand can be used.

The nucleic acid probe used for the measurement of the PPARγ expression-inducing activity is a polynucleotide containing a nucleotide sequence that can hybridize with a transcription product of the PPARγ gene under stringent conditions. The hybridization can be performed by a method known per se or a method similar to such a known method, for example, the methods described in Molecular Cloning, 2nd edition (J. Sambrook et al., Cold Spring Harbor Lab. Press, 1989), and the like. Examples of the stringent conditions include, for example, a hybridization reaction at 45° C. in 6×SSC (sodium chloride/sodium citrate) followed by once or more times of washing in 0.2×SSC/0.1% SDS at 65° C., and the like. Those skilled in the art can adjust the stringency to be a desired stringency by appropriately changing salt concentration of the hybridization solution, temperature for the hybridization reaction, concentration of the probe, length of the probe, number of mismatches, time of the hybridization reaction, salt concentration of the washing solution, temperature for washing, and the like.

The nucleic acid that functions as a probe capable of detecting expression of the PPARγ gene can be obtained by amplifying a nucleic acid of a desired length by PCR using a primer set that is capable of amplifying a part or all of a transcription product of the gene, and as the template, cDNA or genomic DNA derived from any of cells [for example, hepatic cells, splenic cells, nerve cells, glia cells, pancreatic β cells, marrow cells, mesangial cells, Langerhans cells, epidermal cells, epithelial cells, goblet cells, endothelial cells, smooth muscle cells, fibroblasts, fibrocytes, myocytes, fat cells, immunocytes (for example, macrophage, T cell, B cell, natural killer cell, mast cell, neutrophile, basophile, eosinophile, monocyte), megakaryocytes, synovial cells, chondrocytes, osteocytes, osteoblasts, osteoclasts, breast cells, and interstitial cells, or precursor cells, stem cells, or cancer cells of these cells, and the like] or any of tissues in which the foregoing cells exist [for example, brain, parts of brain (for example, olfactory bulb, amygdaloid nucleus, basal ganglia, hippocampus, thalamus, hypothalamus, cerebral cortex, oblongata, cerebellum), spinal cord, pituitary gland, stomach, pancreas, kidney, liver, gonad, thyroid, gallbladder, bone marrow, suprarenal gland, skin, lung, alimentary canal (for example, large intestine, small intestine), blood vessel, heart, thymus gland, spleen, submaxillary gland, peripheral blood, prostate gland, testis, ovary, placenta, uterus, bone, joint, fat tissue, skeletal muscle, and the like] of an individual (for example, human, ape, mouse, rat, dog, bovine, equine, swine, ovine, goat, cat, rabbit, hamster, guinea pig and the like, preferably human), or by cloning the aforementioned gene or cDNA from cDNA or genomic DNA library derived from any of the cells and tissues mentioned above by colony or plaque hybridization, and if necessary, obtaining a fragment of an appropriate length by using a restriction enzyme and the like The hybridization can be performed by, for example, the methods described in Molecular Cloning, 2nd edition (mentioned above), and the like Alternatively, the nucleic acid can be obtained by chemical synthesis of a part or all of the nucleotide sequence and/or a complementary sequence thereof based on the nucleotide sequence information of the aforementioned PPARγ gene, using a commercial automatic DNA/RNA synthesizer. Further, by in situ (on chip) synthesis of the nucleic acid directly on a solid phase such as silicone or glass, a chip on which the nucleic acid is immobilized on a solid phase can also be prepared.

Further, the nucleic acid that functions as a primer that is capable of amplifying a part or all of the transcription product of the PPARγ gene can be obtained by chemical synthesis of a part of the nucleotide sequence and a complementary strand sequence thereof based on the nucleotide sequence information of the aforementioned PPARγ gene, using a commercial automatic DNA/RNA synthesizer.

The nucleic acid is preferably labeled with a labeling agent, in order to make it possible to detect and quantify the target nucleic acid. As the labeling agent, for example, a radioactive isotope, enzyme, fluorescent substance, luminescent substance, and the like are used. As the radioactive isotope, for example, [$^{32}$P], [$^{3}$H], [$^{14}$C], and the like are used. As the enzyme, a stable enzyme showing a high specific activity is preferred, and there are used, for example, β-galactosidase, β-glucosidase, alkaline phosphatase, peroxidase, malate dehydrogenase, and the like. As the fluorescent substance, for example, fluorescamine, fluorescein isothiocyanate, and the like are used. As the luminescent substance, for example, luminol, luminol derivatives, luciferin, lucigenin, and the like are used. Furthermore, biotin-(strept)avidin can be used for the binding of the probe and the labeling agent.

When Northern hybridization is performed, by subjecting an RNA fraction prepared as described above to separation by gel electrophoresis, blotting RNA to a membrane such as cellulose nitrate, nylon, or polyvinylidene difluoride membrane, allowing specific hybridization in a hybridization buffer containing a labeled probe prepared as described above, and then measuring amount of the labeling agent binding to the membrane for each band by an appropriate method, expression amount of the PPARγ gene can be measured. When dot blotting is used, by similarly allowing a hybridization reaction of the RNA fraction spotted on a membrane, and measuring amount of the labeling agent for each spot, expression amount of the gene can be measured.

When DNA chip analysis is used, for example, cDNA introduced with an appropriate promoter such as T7 promoter is synthesized from the RNA fraction prepared as described above by a reverse transcription reaction, and cRNA is further synthesized by using an RNA polymerase (if a mononucleotide labeled with biotin or the like is used as a substrate in this synthesis, a labeled cRNA can be obtained). By contacting labeled cRNAs with the chip on which a probe is immobilized on a solid phase to allow a hybridization reaction, and measuring amounts of labeling agents binding to the probes, expression amount of the PPARγ gene can be measured.

According to another preferred embodiment, the quantitative PCR method is used as the method for measuring expression amount of the PPARγ gene. As the quantitative PCR, for example, competitive PCR, real-time PCR, and the like are available.

Examples of the set of oligonucleotides used as primers in PCR include, for example, nucleic acid primers that enable specific detection of a transcription product of the aforementioned PPARγ gene. In a preferred embodiment, as the set of nucleic acid primers used for the test method of the present invention, examples include a set of oligonucleotides comprising a polynucleotide complementary to a polynucleotide (sense strand) sequence having a length of a contiguous nucleotide sequence containing about 15 or more nucleotides, preferably about 15 to 50 nucleotides, more preferably about 15 to 30 nucleotides, still more preferably about 15 to 25 nucleotides, and designed so that it can amplify a DNA fragment of about 100 bp to several kbp, and a polynucleotide that can hybridize with a polynucleotide (antisense strand) having a nucleotide sequence complementary to the aforementioned polynucleotide sequence.

The competitive RT-PCR means a method of calculating amount of an objective DNA by competitively performing amplification reactions in a reaction mixture also containing, as a competitor, a known amount of another template nucleic acid which can be amplified with a set of primers that can amplify the objective DNA, and comparing amounts of amplified products. Therefore, when the competitive RT-PCR is used, there is used a known amount of a competitor nucleic acid that can be amplified with the aforementioned primer set, of which amplification product can be distinguished (on the basis of, for example, difference of amplified sizes, difference of migration patterns of restriction enzyme-processed fragments observed in electrophoresis, and the like) from the amplification product of the target nucleic acid (namely, transcription product of the nucleotide sequence information on the PPARγ gene) after the amplification, in addition to the aforementioned primer set. The target nucleic acid and the competitor nucleic acid are competitively amplified, since they use the same primers, and therefore the ratio of the amounts of the amplification products reflects the ratio of the amounts of the original templates. The competitor nucleic acid may be DNA or RNA. When the competitor nucleic acid is DNA, after cDNA is synthesized by a reverse transcription reaction from an RNA fraction prepared as described above, PCR can be performed in the presence of the aforementioned primer set and the competitor. When the competitor is RNA, after the competitor is added to an RNA fraction to perform a reverse transcription reaction, the aforementioned primer set can be added to perform PCR. In the latter case, efficiency of the reverse transcription reaction is also taken into consideration, and therefore the absolute amount of the original mRNA can be estimated.

The real-time PCR is a method of monitoring amount of amplification product in real time by using a fluorescent reagent, and requires an apparatus integrally comprising a thermal cycler and a spectrophotofluorometer. Such an apparatus is marketed. Several methods are available in which different fluorescent reagent is used, including, for example, the intercalator method, TaqMan™ probe method, Molecular Beacon method, and the like. In these methods, after cDNA is synthesized by a reverse transcription reaction from an RNA fraction prepared as described above, the aforementioned primer set, SYBR Green I, a reagent that emits fluorescence when it binds with a double-stranded DNA (intercalator), such as ethidium bromide, and a fluorescent regent (probe) comprising a nucleic acid that can be used as the aforementioned probe (the nucleic acid can hybridize to a target nucleic acid in a region to be amplified), of which each end is modified with a fluorescent substance (for example, FAM, HEX, TET, FITC, and the like) or a quenching substance (for example, TAMRA, DABCYL, and the like), e.g. TaqMan™ probe or Molecular Beacon probe, are added to a reaction system for PCR. Since the intercalator emits fluorescence when it binds with a synthesized double-stranded DNA and irradiated with an excitation light, production amount of the amplification product can be monitored by measuring fluorescence intensity, and the amount of the original template cDNA can be thereby estimated. The TaqMan™ probe is an oligonucleotide that can hybridize with the region of the target nucleic acid to be amplified, of which each end is modified with a fluorescent substance or a quenching substance. It hybridizes with the target nucleic acid, but does not emit fluorescence because of the presence of the quenching substance at the time of the annealing, and it is decomposed by exonuclease activity of a DNA polymerase at the time of the extension reaction to release a fluorescent substance, which emits fluorescence. Therefore, by measuring the fluorescence intensity, the production amount of the amplification product can be monitored, and the amount of the original template cDNA can be estimated therefrom. The Molecular Beacon probe is an oligonucleotide that can hybridize with a region of a target nucleic acid to be amplified and can have a hairpin secondary structure, of which both ends are modified with a fluorescent substance and a quenching substance, respectively. When it has the hairpin secondary structure, it does not emit fluorescence because of the presence of the quenching substance, but when it hybridizes with a target nucleic acid at the time of annealing, and thus the distance between the fluorescent substance and the quenching substance increases, it emits fluorescence. Therefore, by measuring the fluorescence intensity, production amount of the amplification product can be monitored, and amount of the original template cDNA can be estimated therefrom. Since the real-time RT-PCR enables real time monitoring of the amount of the product amplified in PCR, it does not require electrophoresis, and thus enables quicker analysis of expression of the PPARγ gene.

Alternatively, expression of the PPARγ gene in a cell can be investigated by preparing a protein fraction from the cell and detecting a translation product of the gene (namely, PPARγ) contained in the fraction. PPARγ can be detected by an immunoassay (for example, ELISA, FIA, RIA, Western blotting, and the like) using antibodies that specifically recognize the protein, or it can be detected by measuring the activity of the protein using a known method. Further alternatively, the protein can also be detected by using mass spectrometry such as MALDI-TOFMS.

The antibody that specifically recognizes PPARγ can be prepared by a general available production method using a polypeptide constituting the protein, total sequence of a partial peptide of the polypeptide showing antigenicity, or a partial peptide thereof corresponding to an epitope as an immunogen. In this specification, examples of the antibody include naturally occurring antibodies such as polyclonal antibodies and monoclonal antibodies (mAb), chimeric antibodies that can be produced by using a gene recombination technique, humanized antibodies, single strand antibodies, and bindable fragments thereof, but not limited to these examples. The antibody is preferably a polyclonal antibody, monoclonal antibodies, or a bindable fragment thereof. The bindable fragment means a partial region of any of the aforementioned antibodies having a specific binding activity, and specific examples thereof include, for example, $F(ab')_2$, Fab', Fab, Fv, sFv, dsFv, sdAb, and the like (Exp. Opin. Ther. Patents, Vol. 6, No. 5, pp. 441-456, 1996). A class of the antibody is not particularly limited, and the antibody may be any of those having any of isotypes such as IgG, IgM, IgA, IgD, or IgE. The antibody is preferably IgG or IgM, and it is more preferably IgG, if easiness of purification and the like are taken into consideration.

When each of the immunoassays is applied to the measurement of the PPARγ expression-inducing activity, setting of special conditions, operations, and the like is not required. A system for measuring PPARγ may be constructed with ordinary conditions and operation methods for each method with usual technical consideration of those skilled in the art. For the details of these general technical means, review articles, published books, and the like can be referred to. For example, "Radioimmunoassay", Edited by H. Irie (Kodansha, 1974), "Radioimmunoassay, Second Series", Edited by H. Irie (Kodansha, 1979), "Enzyme Immunoassay", Edited by E. Ishikawa (Igaku-Shoin, 1978), "Enzyme Immunoassay", 2nd Edition, Edited by E. Ishikawa (Igaku-Shoin, 1982), "Enzyme Immunoassay", 3rd Edition, Edited by E. Ishikawa (Igaku-Shoin, 1987), "Methods in ENZYMOLOGY", Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies)) (these are published by Academic Press), and the like can be referred to.

Further, the PPARγ-agonistic activity can be measured in the same manner as that for the measurement of the PPARγ expression-inducing activity mentioned above, i.e., by preparing an RNA fraction, a protein fraction, or a lipid fraction from a cell, and detecting a transcription product, or a translation product of a gene locating downstream of the PPARγ gene (for example, apoptosis-related gene, fat cell differentiation-related gene, arteriosclerosis-related gene, anti-inflammation-related gene, and the like) or a lipid contained in the fraction. The methods for preparing the RNA fraction and the protein fraction and the methods for detecting them may be the same as the aforementioned methods explained for the measurement of the PPARγ expression-inducing activity. As for the preparation method of a lipid, it may be prepared by using a known method, and there can be used, for example, the Folch method in which a lipid is extracted from a sample containing the lipid by adding several-fold volume of a solvent such as a mixture of chloroform and methanol to the sample, the Bligh-Dyer method in which a lipid is extracted by adding several-fold volume of a solvent such as a mixture of chloroform, methanol and water, or the like. Further, as for the method for detecting the separated lipid, it can be detected by using a known method such as liquid chromatography (LC), gas chromatography (GC), and high performance liquid chromatography (HPLC). Alternatively, a method of directly detecting a lipid contained in a fat cell or tissue may also be used. The reagents and the like usable for such a method are marketed, and for example, HCS LipidTOX Phospholipidosis and Steatosis Detection Kit (Invitrogen) and the like can be used.

Examples of person to whom the prophylactic or therapeutic agent of the present invention for giant cell tumors occurring in a bone and soft tissue or for chondrosarcoma can be applied, which agent comprises a substance having a PPARγ expression-inducing activity and has a PPARγ-agonistic activity used in the present invention, preferably a non-steroidal anti-inflammatory agent or a thiazolidine derivative, as an active ingredient, include, for example, a person who has clinically diagnosed to have giant cell tumor occurring in a bone and soft tissue or have chondrosarcoma, a person suspected to be that mentioned above, and a person for whom onset of such a disease as mentioned above is expected. Further, the therapeutic agent of the present invention can also be preferably applied to a metastatic cancer of which primary lesion is giant cell tumors occurring in a bone and soft tissue or chondrosarcoma. Examples of such metastatic cancer include those of lung cancer, colon cancer, breast cancer, prostate cancer, esophageal cancer, gastric cancer, liver cancer, biliary carcinoma, spleen carcinoma, renal carcinoma, vesical cancer, uterine cancer, ovarian cancer, testis cancel, thyroid gland cancer, pancreatic cancer, brain tumor, blood tumor, and the like.

The prophylactic or therapeutic agent for giant cell tumors occurring in a bone and soft tissue or for chondrosarcoma of the present invention can be orally used in the form of a tablet, which may have a sugar coating as required, capsule, elixir, microcapsule, or the like, or can be parenterally used in the form of an injection such as a sterile solution or suspension in water or another pharmacologically acceptable solvent. The prophylactic or therapeutic agent can be prepared by forming a mixture together with physiologically acceptable carrier, flavoring agent, excipient, vehicle, preservative, stabilizer, binder, and the like in the form of a generally acceptable unit dosage form required for implementation of pharmaceutical preparation. Amount of the active ingredient in such a preparation as mentioned above is appropriately chosen by taking a dose into consideration, which will be described later.

As additives that can be mixed in tablets, capsules, and the like, there are used, for example, binders such as gelatin, cornstarch, tragacanth, and gum arabic, excipients such as crystalline cellulose, bulking agents such as cornstarch, gelatin, and alginic acid, lubricants such as magnesium stearate, sweeteners such as sucrose, lactose, and saccharin, flavoring agents such as peppermint, Gaultheria adenothrix oil, and cherry, and the like. When a unit dosage form is a capsule, liquid carriers such as oil or fat may further be added to the aforementioned materials. A sterilized composition used for injection can be formulated by a common pharmaceutical manufacturing method, such as a method of allowing the active ingredient to exist in a vehicle such as a distilled water for injection, or a method of dissolving or suspending the active ingredient in a naturally produced vegetable oil such as sesame oil and coconut oil.

Examples of an aqueous solution used for injection include physiological saline, an isotonic solution comprising glucose or other auxiliary agents (for example, D-sorbitol, D-mannitol, sodium chloride, and the like), and the like. Such aqueous solution may also be used in combination with appropriate solubilizing aids including alcohols (for example, ethanol, and the like), polyalcohols (for example, propylene glycol, polyethylene glycol, and the like), or nonionic surfactants (for example, Polysorbate 80™, HCO-50, and the like). Examples of oily liquid include sesame oil and soybean oil, and such oily liquid may be used in combination with a solubilizing aid such as benzyl benzoate or benzyl alcohol. In addition, a buffer (for example, phosphate buffer, sodium acetate buffer, and the like), soothing agent (for example, benzalkonium chloride, procaine hydrochloride, and the like), stabilizer (for example, human serum albumin, polyethylene glycol, and the like), preservative (for example, benzyl alcohol, phenol, and the like), antioxidant, and the like may also be mixed. The prepared injection is usually filled into a suitable ampoule.

The pharmaceutical preparation obtained as described above is safe with reduced toxicity, and therefore it can be administered to, for example, mammals (for example, human, rat, mouse, guinea pig, rabbit, ovine, swine, bovine, equine, cat, dog, ape, and the like).

Although a dose of the prophylactic or therapeutic agent for giant cell tumors occurring in a bone and soft tissue or for chondrosarcoma according to the present invention may differ depending on severity of the giant cell tumor occurring in a bone and soft tissue or that of chondrosarcoma, an object of administration, an administration route and the like, the dose may be, for example, in the case of oral administration, generally about 0.1 to 100 mg, preferably about 1.0 to 50 mg, more preferably about 1.0 to 20 mg, per day for an adult (body weight, 60 kg). In the case of parenteral administration, the dose of the prophylactic or therapeutic agent may also differ depending on an object of administration, severity, and the like. When the agent is administered to an adult (body weight, 60 kg) as an injection, the dose may be, for example, about 0.01 to 30 mg, preferably about 0.1 to 20 mg, more preferably about 0.1 to 10 mg, per day. Also when the object of the administration is an animal, not a human, the agent can be administered at a dose determined from a dose per unit body weight calculated from the aforementioned dose per 60 kg of body weight.

So far, the mainstream of the method for therapeutic treatment of osteoclastoma has been extraction of lesion by a surgical operation, and the therapeutic treatment is performed by curetting the tumor in a lesion, and filling a bone lacking part with an allogeneic bone, autogenous bone or artificial bone. However, such a method results in high recurrence rate of the tumor, and suffers from risks of metastasis or malignant transformation in the process of repetition of recurrence. By adding the substance having a PPARγ expression-inducing activity and a PPARγ-agonistic activity according to the present invention, preferably a non-steroidal anti-inflammatory agent or thiazolidine derivative, to artificial bone used for restoration of a bone lacking part, giant cell tumor recurrence-preventing effect can be expected. Therefore, the present invention provides an artificial bone containing a substance having a PPARγ expression-inducing activity and a PPARγ-agonistic activity, preferably a non-steroidal anti-inflammatory agent or thiazolidine derivative.

As the substance having a PPARγ expression-inducing activity and a PPARγ-agonistic activity, contained in the artificial bone of the present invention, preferably a non-steroidal anti-inflammatory agent or thiazolidine derivative, those mentioned above can be used.

Examples of the material used for the artificial bone of the present invention include known biomaterials for orthopedic surgery, for example, metallic materials, ceramic materials, polymer materials, protein materials, and composite materials of these.

Examples of the aforementioned metallic substances include, for example, titanium, titanium alloy, stainless steel, cobalt-chrome alloy, and the like.

Examples of the aforementioned ceramic materials include, for example, bio-inert ceramics such as alumina ceramics, single crystal alumina ceramics, and zirconia ceramics, and bio-active ceramics such as bioglass (Hench et al., Biomed. Master. Symp., 2, 117 (1972)), hydroxyapatite (Aoki et al., Ceramics, 10, 469 (1975)), apatite-wollastonite (AW) glass (Bull. Inst. Chem. Res. KyotoUni., 60, 260 (1982)), and TCP ceramics ($Ca_3(PO_4)_2$).

Examples of the aforementioned polymer materials include, for example, poly(methyl methacrylate) (PMMA), high density polyethylene (HDP), silicone rubber, Teflon, polyester, polylactic acid, PVA hydrogel, and the like.

Examples of the aforementioned protein materials include, for example, collagen, fibrin, chitin, chitosan, and the like.

Ratio of the substance having a PPARγ expression-inducing activity and having a PPARγ-agonistic activity, preferably a non-steroidal anti-inflammatory agent or thiazolidine derivative, in the artificial bone of the present invention consisting of a mixture of the substance having a PPARγ expression-inducing activity and having a PPARγ-agonistic activity, preferably a non-steroidal anti-inflammatory agent or thiazolidine derivative, and an artificial bone material, or an artificial bone material coated with the substance is about 1 to 20%, preferably about 15 to 20%.

As described above, the inventors of the present invention found that a specific compound having a PPARγ-agonistic activity induced expression of PPARγ in giant cell tumors occurring in a bone and soft tissue or chondrosarcoma, and simultaneously induced apoptosis or fat cell differentiation. Therefore, the present invention also provides a method of screening a prophylactic or therapeutic agent for giant cell tumors occurring in a bone and soft tissue or chondrosarcoma.

The method of screening a prophylactic or therapeutic agent for giant cell tumors occurring in a bone and soft tissue or chondrosarcoma of the present invention comprises the following steps:

(1) the step of culturing a cell derived from giant cell tumors occurring in a bone and soft tissue or chondrosarcoma under each condition of presence or absence of a test substance,
(2) the step of measuring expression of the PPARγ gene, and also measuring
(i) expression of an apoptosis-related gene, or
(ii) expression of a fat cell differentiation-related gene under both the conditions, and
(3) the step of selecting a test substance that significantly changes expression of the PPARγ gene, and also significantly changes
(i) expression of an apoptosis-related gene, or
(ii) expression of a fat cell differentiation-related gene, compared with those observed under the condition of absence of the test substance.

The cell derived from giant cell tumors occurring in a bone and soft tissue or chondrosarcoma used in the screening method of the present invention may be a primary cultured cell derived from a patient clinically diagnosed to have giant cell tumor occurring in a bone and soft tissue or chondrosarcoma, or a cell of an already established cell line. A cell line can be established according to a method ordinarily performed in this field, or according to a description of published references. Further, the cell derived from giant cell tumors occurring in a bone and soft tissue or from chondrosarcoma may consist of an arbitrary tissue (for example, synovial membrane, joint, cartilage, and the like) containing the cells, and such tissue, organ, or the like may be isolated from a living body and cultured. After a test substance is administered to a living body per se, a biosample may be isolated after a certain period of time.

In the screening method of the present invention, when the cell derived from giant cell tumors occurring in a bone and soft tissue or from chondrosarcoma is a cultured cell, the cell is cultured in the presence or absence of a test substance.

According to the present invention, the test substance is not particularly limited, and there are used, for example, a peptide, protein, non-peptide compound, synthetic compound, fermentation product, cell extract, plant extract, animal tissue extract, or the like is used, and these compounds may be novel compounds or known compounds. It is preferred and expected that the test substance is a substance having a PPARγ expression-inducing activity and having a PPARγ-agonistic activity. Examples of such test substance include non-steroidal anti-inflammatory agents. Examples of the non-steroidal anti-inflammatory agents include zaltoprofen, diclofenac, indomethacin, and the like as mentioned above. Besides the non-steroidal anti-inflammatory agents, examples include, for example, thiazolidine derivatives, as mentioned above. Examples of the thiazolidine derivatives include, for example, rosiglitazone, pioglitazone, troglitazone, balaglitazone, rivoglitazone, and the like.

The culture can be performed on an appropriate cell culture base material, and examples of the base material include, for example, flask, flask for tissue culture, dish, petri dish, dish for tissue culture, multidish, microplate, microwell plate, multiplate, multiwell plate, chamber slide, petri dish, tube, tray, culture bag, and roller bottle.

Cells derived from giant cell tumors occurring in a bone and soft tissue or chondrosarcoma and suspended as monocells can be suspended in a medium, and inoculated on the aforementioned cell culture base material. The cells are usually cultured in an incubator maintained at 5% $CO_2$/95% air and 37° C. until the cells reach confluent.

When expressions of the PPARγ gene and an apoptosis-related gene are measured, a test substance and the cells can be contacted by for example, contacting a medium suitable for apoptosis of the cells (for example, minimum essential medium (MEM), Dulbecco's modified Eagle's medium (DMEM), RPMI1640 medium, 199 medium, F12 medium, and the like containing about 5 to 20% of fetal bovine serum (FBS)) and any of various buffers (for example, HEPES buffer, phosphate buffer, phosphate buffered saline, Tris-HCl buffer, borate buffer, acetate buffer, and the like) containing the test substance with the cells for a certain period of time. Although concentration of the test substance to be added should be changed depending on the type of the compound (solubility, toxicity, and the like), the concentration is appropriately chosen to be in the range of, for example, about 1 to 1000 μM, preferably about 5 to 500 μM, more preferably about 50 to 200 μM. Time of the contact is, for example, about 1 to 48 hours, preferably about 5 to 36 hours, more preferably about 10 to 24 hours. Further, when expressions of the PPARγ gene and a fat cell differentiation-related gene or a lipid are measured, a test substance and the cells can be contacted for a certain period of time, for example, by adding the test substance in a serum free medium suitable for fat cell differentiation of the cells (for example, minimum essential medium (MEM), Dulbecco's modified Eagle's medium (DMEM), RPMI1640 medium, 199 medium, F12 medium, and the like) and any of various buffers (for example, HEPES buffer, phosphate buffer, phosphate buffered saline, Tris-HCl buffer, borate buffer, acetate buffer, and the like). The aforementioned medium may optionally contain blood serum (for example, about 5 to 20% of fetal bovine serum (FBS)), and a fat cell inducing aid (for example, isobutyl-methylxanthine (IBMX), dexamethasone, insulin, and the like) as required. Furthermore, examples of other additives include transferrin, T3, cortisol, asc, calcium pantothenate, biotin, and the like. Further, a commercially available known kit for fat cell differentiation may also be used. Although concentration of the test substance to be added should be changed depending on the type of the compound (solubility, toxicity, and the like), the concentration is appropriately chosen to be in the range of, for example, about 1 to 1000 μM, preferably about 5 to 500 μM, more preferably about 50 to 200 μM. Time of the contact is, for example, about 1 to 48 hours, preferably about 5 to 36 hours, more preferably about 10 to 24 hours. For inducing fat cell differentiation, the cells may be cultured in a fat cell differentiation-inducing medium, while they are contacted with a test substance, or the cells may be contacted with a test substance for a certain period of time, and then cultured in a fat cell differentiation-inducing medium.

In the screening method of the present invention, together with expression of the PPARγ gene, (i) expression of an apoptosis-related gene, or (ii) expression of a fat cell differentiation-related gene is measured in the presence or absence of a test substance. Expression of the PPARγ gene can be measured by the aforementioned method for measuring the PPARγ expression-inducing activity. Further, expressions of an apoptosis-related gene, a fat cell differentiation-related gene, and a lipid can also be measured by the aforementioned method for measuring the PPARγ-agonistic activity.

As shown in the examples below, expression of PPARγ was not observed in giant cell tumor occurring in a bone and soft tissue or in chondrosarcoma. Further, when a non-steroidal anti-inflammatory agent or thiazolidine derivative having a PPARγ-agonistic activity was administered or contacted, induced expression of PPARγ could be confirmed. Furthermore, together with the induced expression, expression of caspase 3 or a lipid could be confirmed.

Therefore, in the aforementioned screening, a prophylactic or therapeutic agent for giant cell tumors occurring in a bone and soft tissue or chondrosarcoma that can induce apoptosis or fat cell differentiation mediated by PPARγ in giant cell tumors occurring in a bone and soft tissue or in chondrosarcoma can be selected.

When a relatively higher (or lower) expression level of the PPARγ gene or a lipid is observed in the cells administered with a test substance compared with the cells not administered with the test substance in the results of comparison of expression levels of the PPARγ gene, as well as an apoptosis-related gene, a fat cell differentiation-related gene, and a lipid, the test substance can be selected as a prophylactic or therapeutic agent for giant cell tumors occurring in a bone and soft tissue or for chondrosarcoma, which exhibits PPARγ-mediated efficacy thereof. For example, it is sufficient that the test substance provides a statistically significant difference compared with the result obtained in the absence of the test substance, and a test substance that increases (or decreases) the expression amount of the PPARγ gene, an apoptosis-related gene, a fat cell differentiation-related gene, or a lipid by about 20% or more, preferably about 30% or more, more preferably about 50% or more, can be chosen as a prophylactic or therapeutic agent for giant cell tumors occurring in a bone and soft tissue or for chondrosarcoma.

EXAMPLES

Hereafter, the present invention will be explained with reference to examples and reference examples. However, the present invention is not limited by the examples.

Example 1: Analysis of Suppression of Cell Proliferation and Apoptosis of Cultured Cells of Osteoclastoma (GCT) Observed after Addition of Zaltoprofen GCT cultured cells (case 1, patient with osteoclastoma in a distal part of the right femur, in twenties; case 2, patient with osteoclastoma in a distal part of the right femur, in twenties) were cultured on a 96-well culture plate, zaltoprofen was added to the cells at various concentrations (5, 10, 50, 100, and 200 μM), color development was attained with Cell Counting Kit-8 (CCK-8) (Dojindo) 24 hours thereafter, and absorbance was measured at 450 nm 3 hours thereafter (FIG. 1). As a result, zaltoprofen concentration-dependent suppression of the cell proliferation was successfully observed.

Further, the aforementioned GCT cultured cells of the case 1 were cultured on chamber cover slide glass, and zaltoprofen was added at different concentrations (100, and 200 μM) 24 hours afterward. Then, 8 hours and 24 hours afterward, the cells were fixed with 4% paraformaldehyde, staining with caspase 3 and Tunel assay were performed, and presence or absence of apoptosis was analyzed. Observation was performed with a fluorescence microscope (BZ-9000) of Keyence, and positive images for each concentration were quantitatively observed (FIGS. 2 to 5). As a result, zaltoprofen concentration and administration time-dependent increases of the Tunel-positive ratio and caspase 3-positive ratio were successfully observed.

Figure 6:
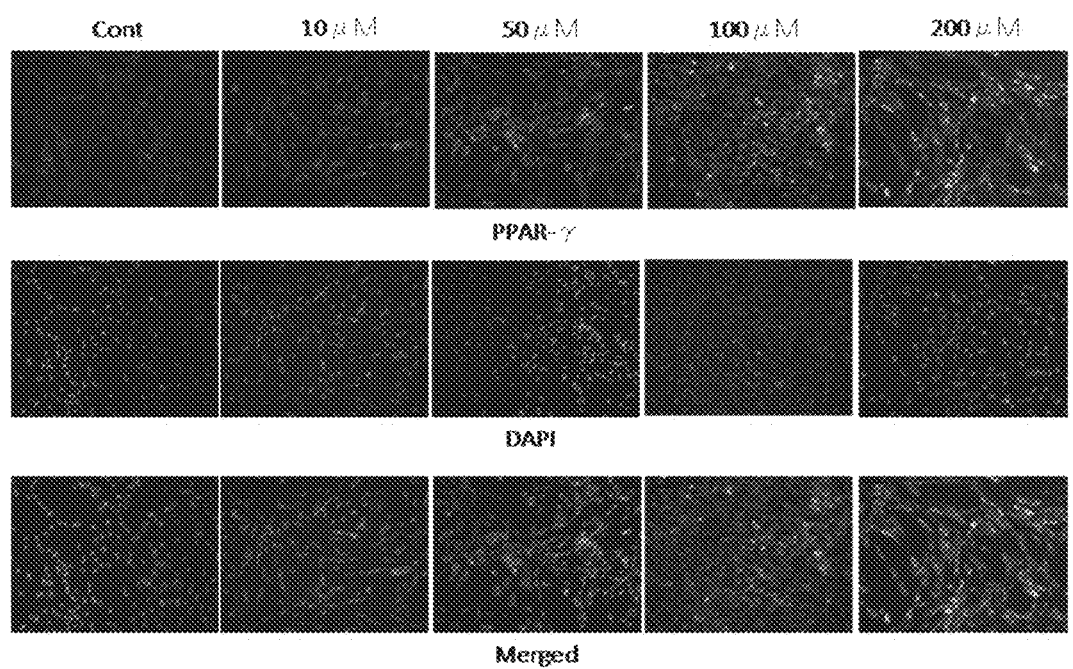
FIG. 6 Photographs showing results of PPARγ staining of GCT cultured cells that were cultured in a zaltoprofen-containing medium.
Figure 7:
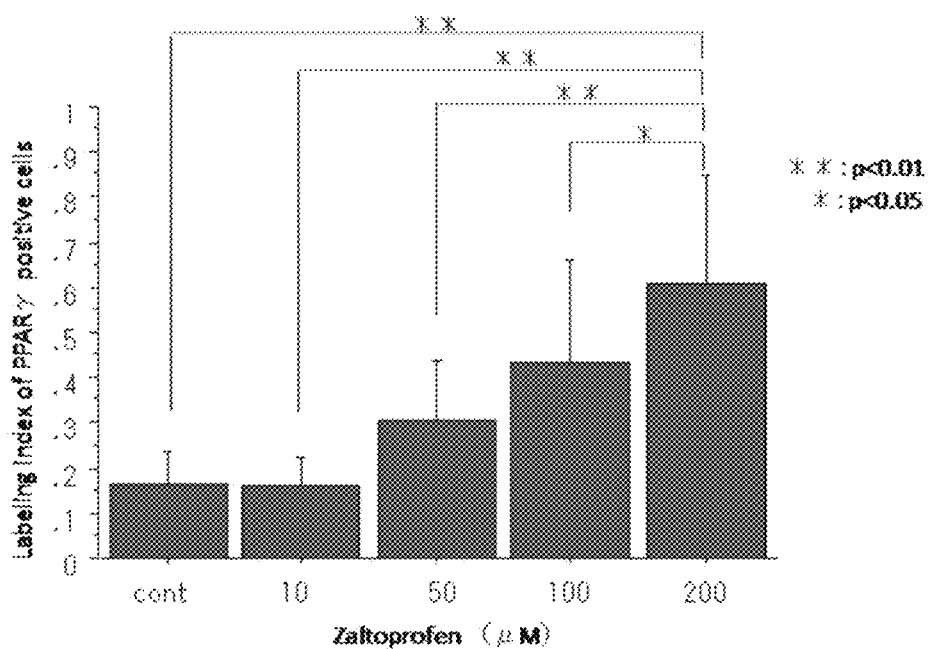
FIG. 7 A graph showing ratios of PPARγ-positive cells in GCT cultured cells that were cultured in a zaltoprofen-containing medium.

Example 2: PPARγ Immunostaining of Cultured Cells of Osteoclastoma (GCT) Performed after Addition of Zaltoprofen The GCT cultured cells of the aforementioned case 1 were cultured on chamber cover slide glass, and 24 hours thereafter, zaltoprofen was added at various concentrations (10, 50, 100, and 200 μM). After 24 hours, the cells were fixed with 4% paraformaldehyde, and staining of PPARγ was performed. Observation was performed with a fluorescence microscope (BZ-9000) of Keyence, and positive images for each concentration were quantitatively observed (FIGS. 6 and 7). As a result, it was successfully observed that the expression of PPARγ was about 15% for the control, and the expression of PPARγ was increased in a zaltoprofen concentration-dependent manner.

Figure 8:
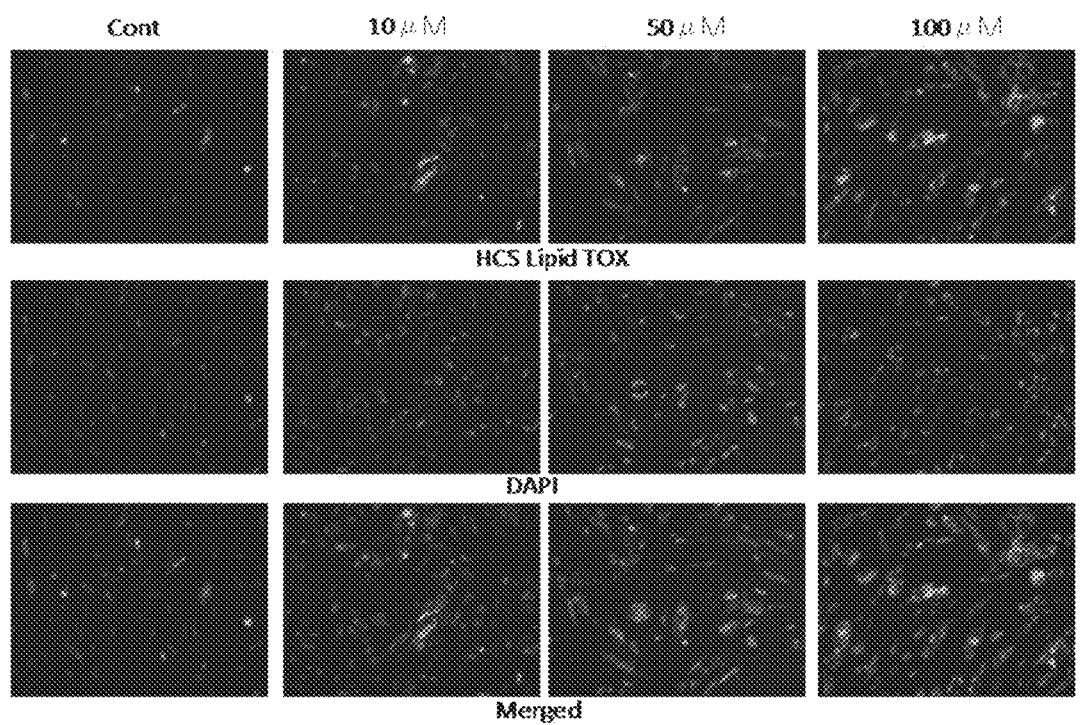
FIG. 8 Photographs showing results of lipid staining of GCT cultured cells that were cultured in a zaltoprofen-containing medium.
Figure 9:
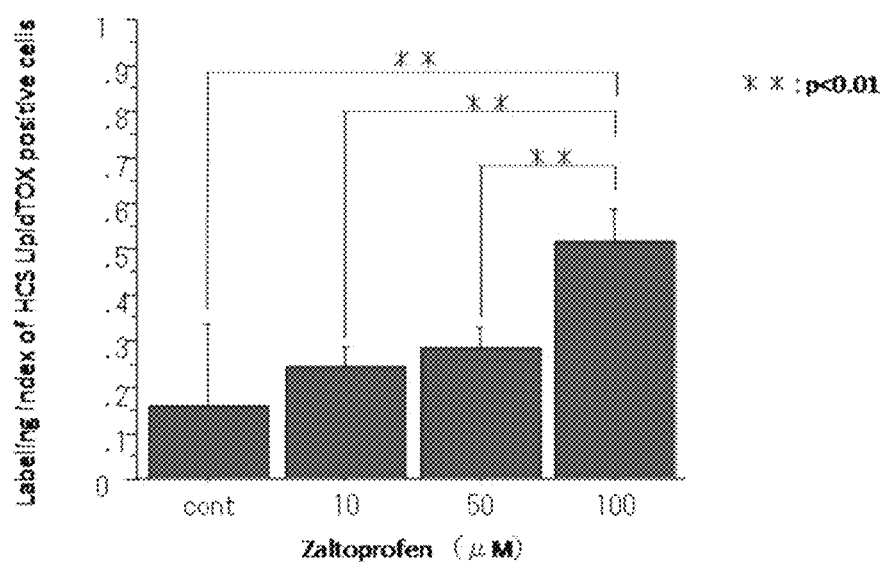
FIG. 9 A graph showing ratios of lipid-positive cells in GCT cultured cells that were cultured in a zaltoprofen-containing medium.

Example 3: Analysis of Fat Cell Differentiation of Cultured Cells of Osteoclastoma (GCT) Observed after Addition of Zaltoprofen It has been reported that PPARγ is a transcription factor indispensable for fat cell differentiation. Therefore, the GCT cultured cells of the aforementioned case 1 were cultured on chamber cover slide glass, and when they reached confluent, zaltoprofen was added to the cells at various concentrations (10, 50, and 100 μM). From 24 hours thereafter, the cells were cultured in a fat cell differentiation-inducing medium (STREMPRO Adipogenesis Differentiation Kit, Invitrogen) for 7 to 14 days, and differentiation into fat cells was analyzed with HCS LipidTOX Green Neutral Lipid Stain (Invitrogen) (FIGS. 8 and 9). As a result, it was successfully observed that only a few positive images were obtained with HCS LipidTOX Green Neutral Lipid Stain for the control, but positive images obtained with HCS LipidTOX Green Neutral Lipid Stain were increased in a zaltoprofen concentration-dependent manner.

Figure 10:
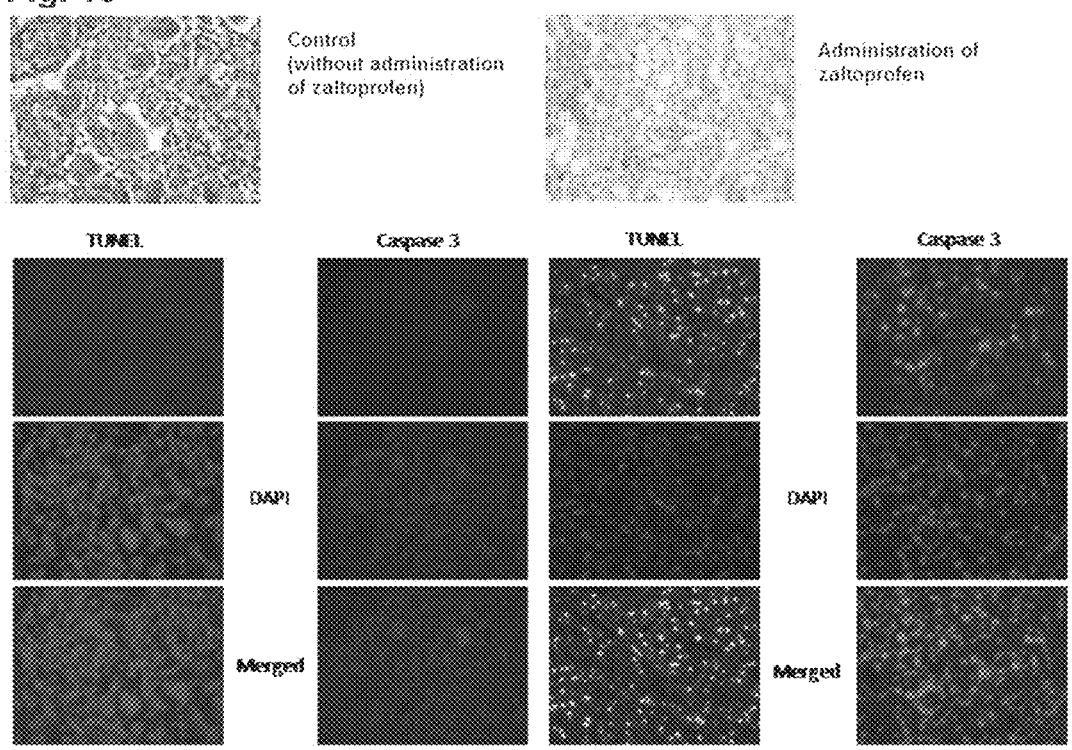
FIG. 10 Photographs showing results of Tunel assay and caspase 3 staining of GCT samples derived from a GCT patient administered with zaltoprofen.

Example 4: Analysis of Apoptosis of Cells Derived from Patient with Osteoclastoma (GCT) Administered with Zaltoprofen An operational excision sample of a man in his 30's who had been administered with 3 tablets per day of the zaltoprofen tablets, Soleton Tablet 80 (generic name: zaltoprofen, 80 mg, Nippon Chemiphar) for about 28 days for pain due to the tumor, and then subjected to the operation, and an operational excision sample of a patient with osteoclastoma not administered with zaltoprofen as a control were subjected to caspase 3 staining and Tunel assay, and analyzed for the presence or absence of apoptosis. Observation was performed with a fluorescence microscope (BZ-9000) produced by Keyence (FIG. 10). As a result, almost no Tunel-positive cells and caspase 3-positive cells were observed among the cells derived from the GCT patient not administered with zaltoprofen, whilst Tunel-positive cells and caspase 3-positive cells were observed among the cells derived from the patient administered with zaltoprofen.

Figure 11:
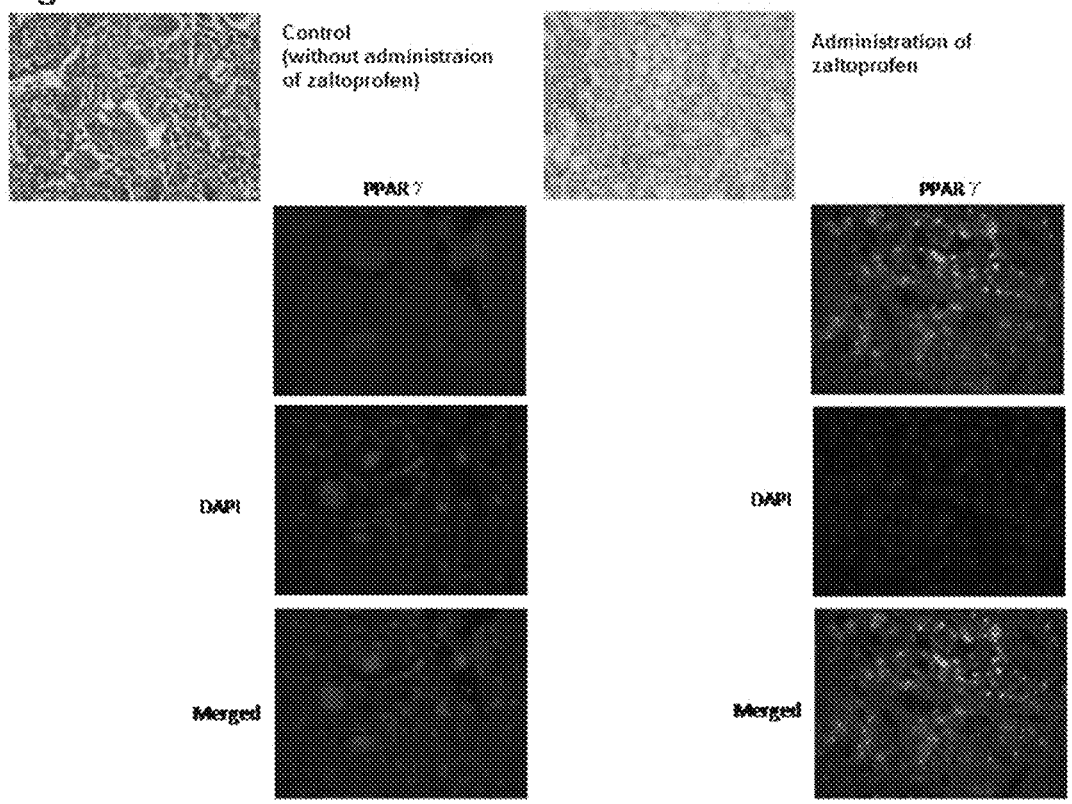
FIG. 11 Photographs showing results of PPARγ staining of GCT samples derived from a GCT patient administered with zaltoprofen.

Example 5: PPARγ Immunostaining of Cells Derived from Patient with Osteoclastoma (GCT) Administered with Zaltoprofen An operational excision sample of a man in his 30's who had been administered with 3 tablets per day of the zaltoprofen tablets, Soleton Tablet 80 (generic name: zaltoprofen, 80 mg, Nippon Chemiphar) for about 28 days for pain due to the tumor, and then subjected to the operation, and an operational excision sample of a patient with osteoclastoma not administered with zaltoprofen as a control were subjected to staining of PPARγ, and expression of PPARγ was analyzed. Observation was performed with a fluorescence microscope (BZ-9000) of Keyence (FIG. 11). As a result, almost no PPARγ-expressing cells were observed among the cells derived from the GCT patient not administered with zaltoprofen, whilst PPARγ-expressing cells were observed among the cells derived from the patient administered with zaltoprofen, and in addition fat cell differentiation was observed.

Figure 12:
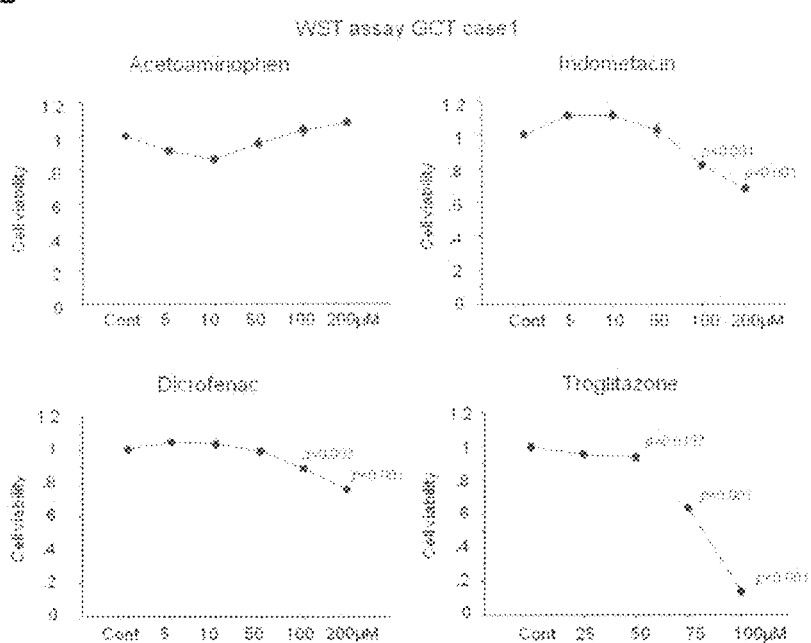
FIG. 12 Graphs showing results of suppression of proliferation of GCT cultured cells that were cultured in an acetaminophen, indomethacin, diclofenac, or troglitazone-containing medium.
Figure 13:
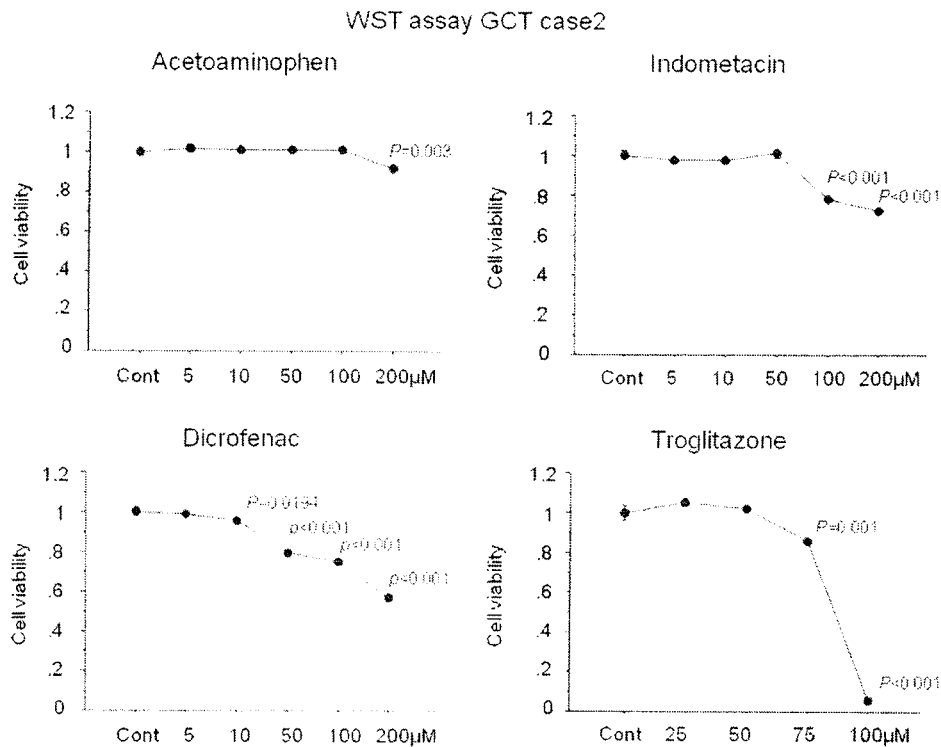
FIG. 13 Graphs showing results of suppression of proliferation of GCT cultured cells that were cultured in an acetaminophen, indomethacin, diclofenac, or troglitazone-containing medium.

Example 6: Analysis of Suppression of Cell Proliferation of Cultured Cells of Osteoclastoma (GCT) Observed after Addition of Non-Steroidal Anti-Inflammatory Agent In the same manner as that of Example 1, the GOT cultured cells (case 1, case 2) were cultured, a non-steroidal anti-inflammatory agent (acetaminophen, indomethacin, or diclofenac) or troglitazone was added at various concentrations, and absorbance was measured at 450 nm (FIGS. 12 and 13). As a result, it was observed that the proliferation of cells was suppressed in a non-steroidal anti-inflammatory agent concentration-dependent manner.

Figure 14:
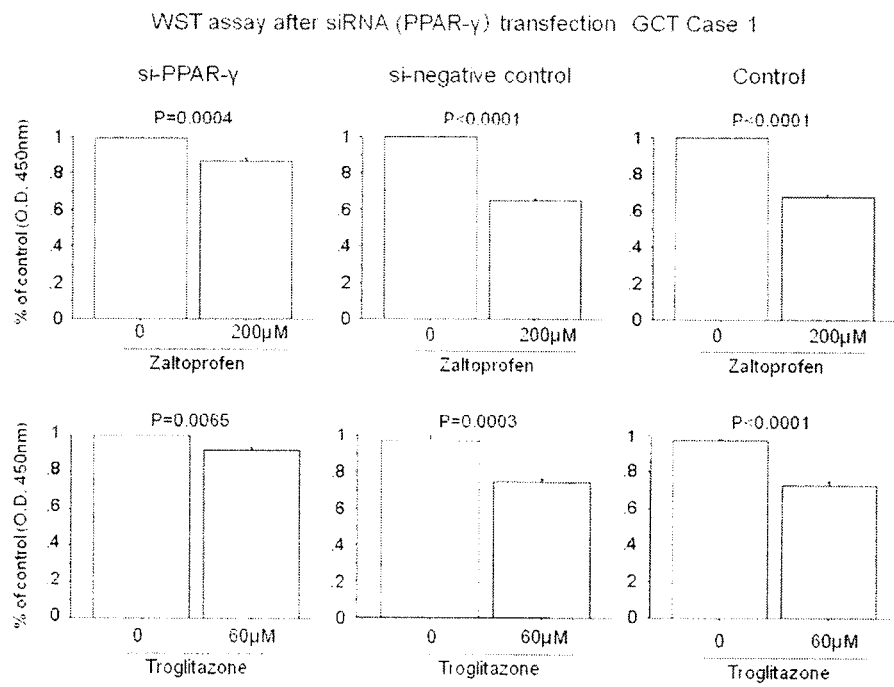
FIG. 14 Graphs showing effect of PPARγ siRNA on GCT cultured cells that were cultured in a zaltoprofen or troglitazone-containing medium.
Figure 15:
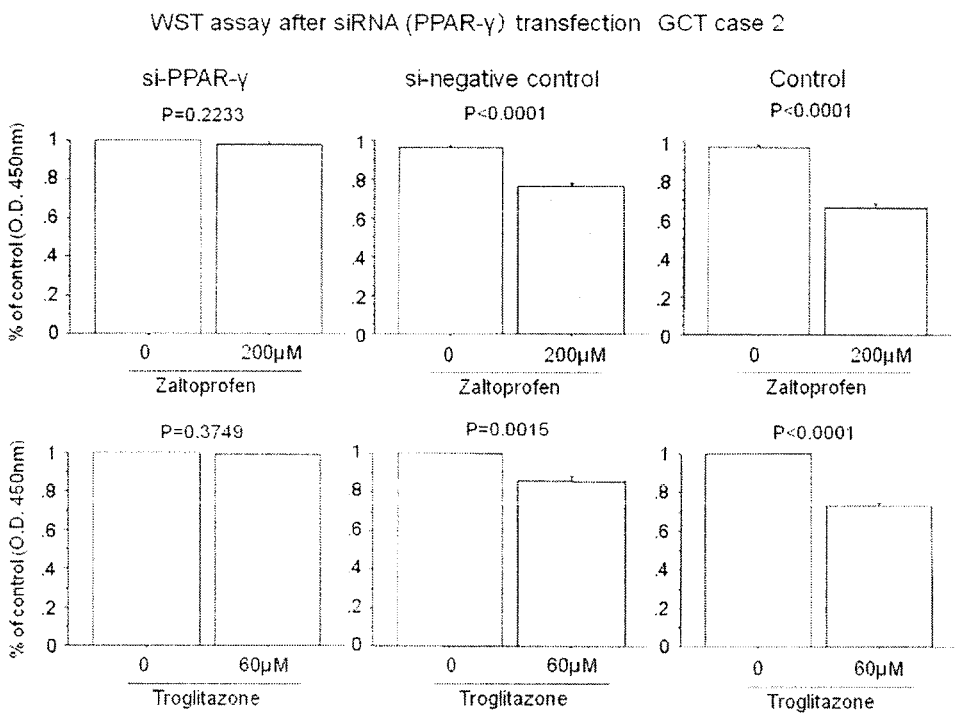
FIG. 15 Graphs showing effect of PPARγ siRNA on GCT cultured cells that were cultured in a zaltoprofen or troglitazone-containing medium.

Example 7: Effect of PPARγ siRNA on Cultured Cells of Osteoclastoma (GOT) Observed after Addition of Non-Steroidal Anti-Inflammatory Agent The cells (case 1, case 2) were cultured on a 96-well culture plate, allowed to react with PPARγ siRNA, negative control siRNA, or only with the transfection reagents (Thermo Scientific DharmaFECT, Thermo Scientific) for 48 hours, and further cultured in a usual culture medium for 48 hours. Then, 200 μM of zaltoprofen or 60 μM of troglitazone was added to the cells, 72 hours thereafter, color development was performed with Cell Counting Kit-8 (CCK-8, Dojindo), and 3 hours thereafter, absorbance was measured at 450 nm (FIGS. 14 and 15). As a result, it was observed that the effect of zaltoprofen was significantly suppressed in the PPARγ siRNA addition group.

Figure 16:
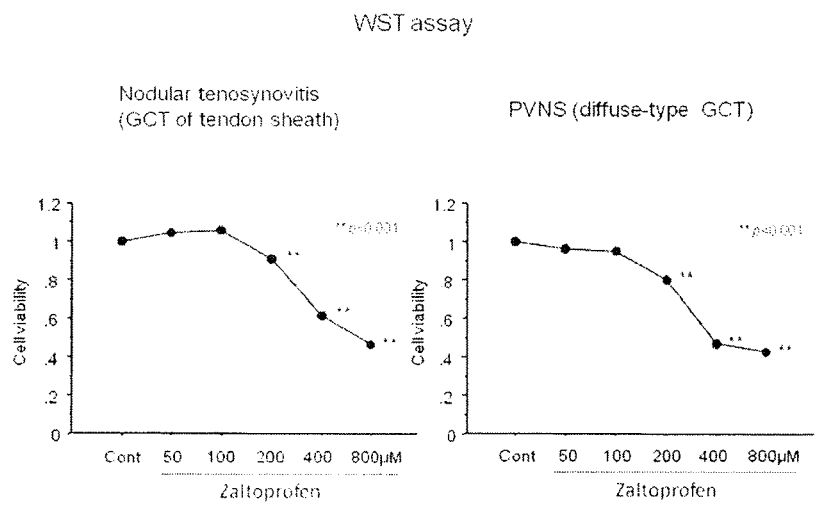
FIG. 16 Graphs showing results of suppression of proliferation of cultured cells derived from giant cell tumor of tendon sheath or cultured cells derived from pigmented villonodular synovitis cultured in a zaltoprofen-containing medium.
Figure 17:
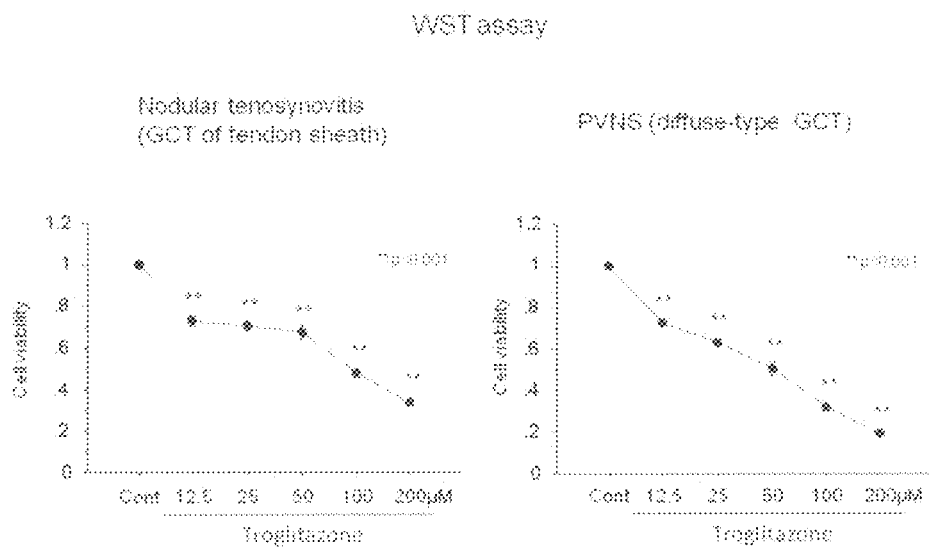
FIG. 17 Graphs showing results of suppression of proliferation of cultured cells derived from giant cell tumor of tendon sheath or cultured cells derived from pigmented villonodular synovitis cultured in a troglitazone-containing medium.
Figure 18:
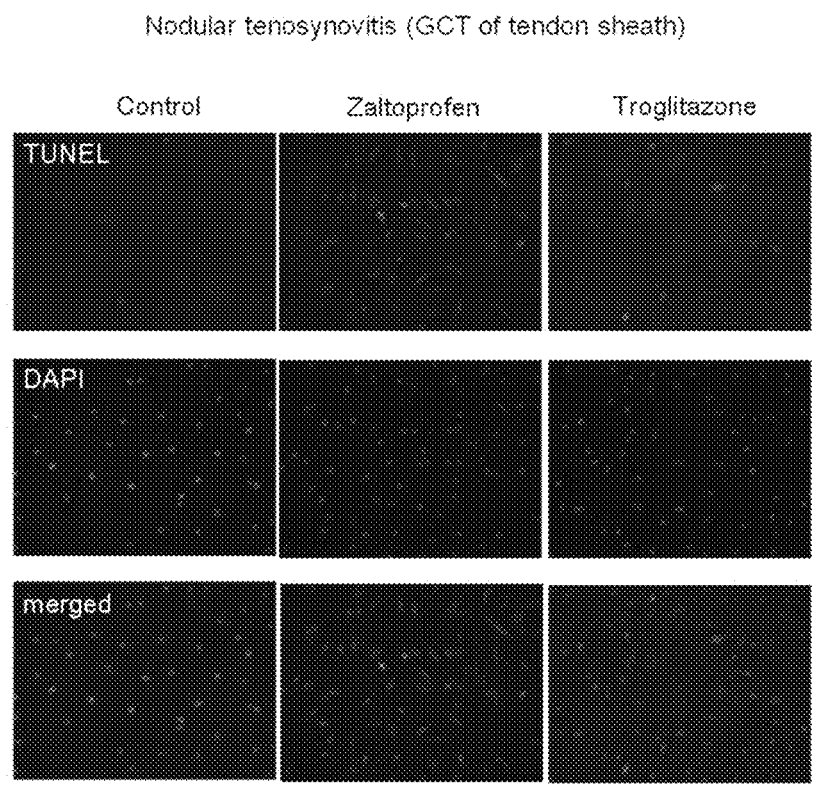
FIG. 18 Photographs showing results of Tunel assay of cultured cells derived from giant cell tumor of tendon sheath cultured in a zaltoprofen or troglitazone-containing medium.
Figure 19:
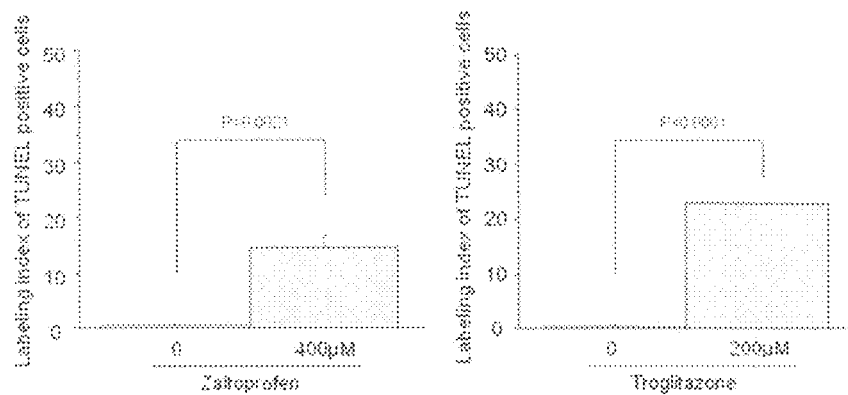
FIG. 19 Graphs showing ratios of Tunel-positive cells in cultured cells derived from giant cell tumor of tendon sheath cultured in a zaltoprofen or troglitazone-containing medium.
Figure 20:
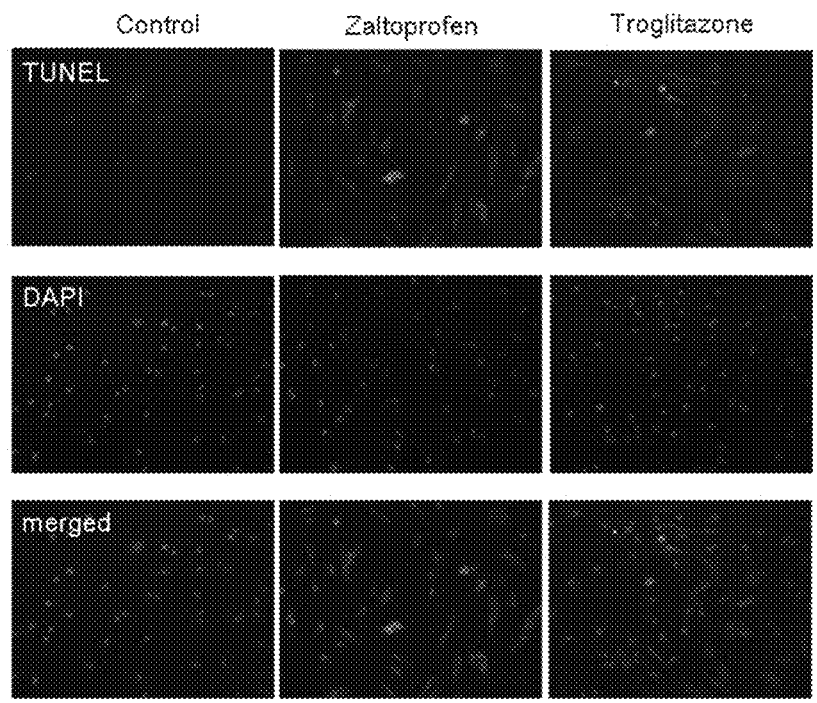
FIG. 20 Photographs showing results of Tunel assay of cultured cells derived from pigmented villonodular synovitis cultured in a zaltoprofen or troglitazone-containing medium.
Figure 21:
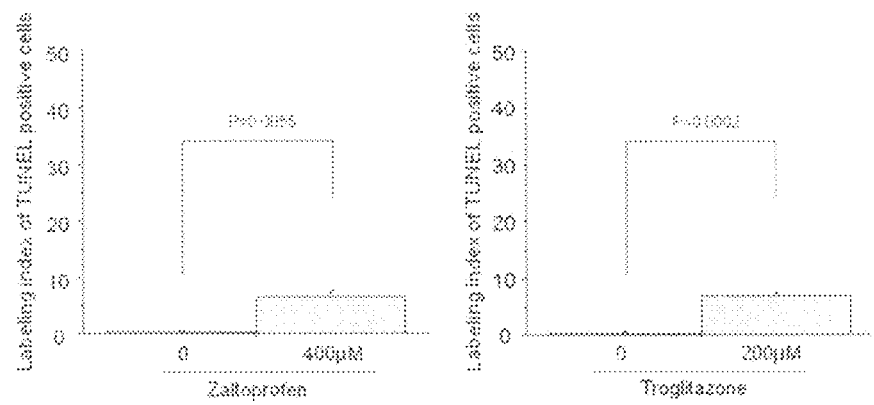
FIG. 21 Graphs showing ratios of Tunel-positive cells in cultured cells derived from pigmented villonodular synovitis cultured in a zaltoprofen or troglitazone-containing medium.
Figure 22:
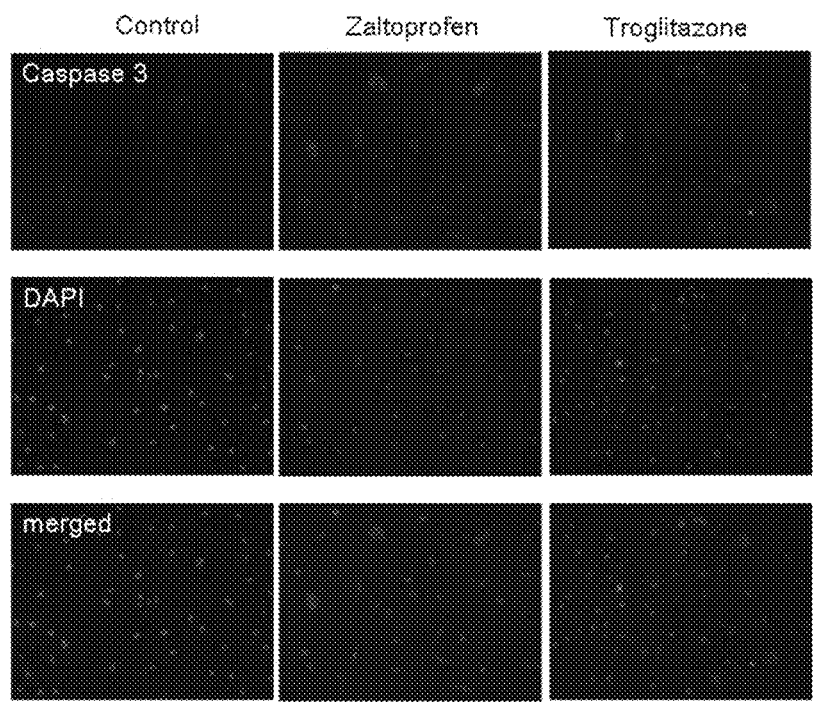
FIG. 22 Photographs showing results of caspase 3 staining of cultured cells derived from giant cell tumor of tendon sheath cultured in a zaltoprofen or troglitazone-containing medium.
Figure 23:
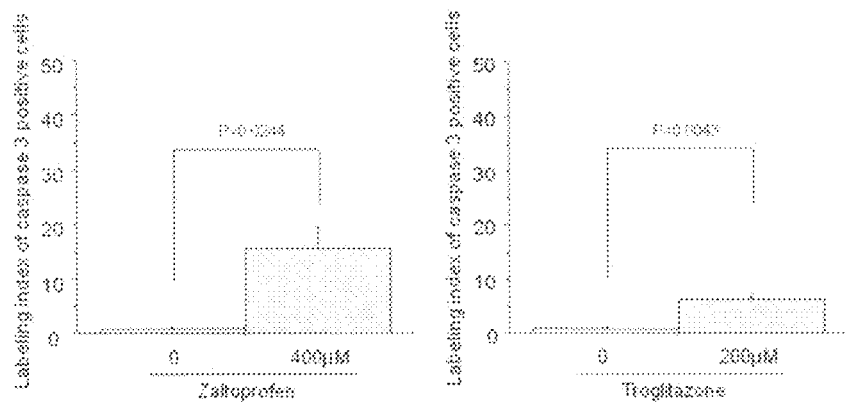
FIG. 23 A graph showing ratios of caspase 3-positive cells in cultured cells derived from giant cell tumor of tendon sheath cultured in a zaltoprofen or troglitazone-containing medium.
Figure 24:
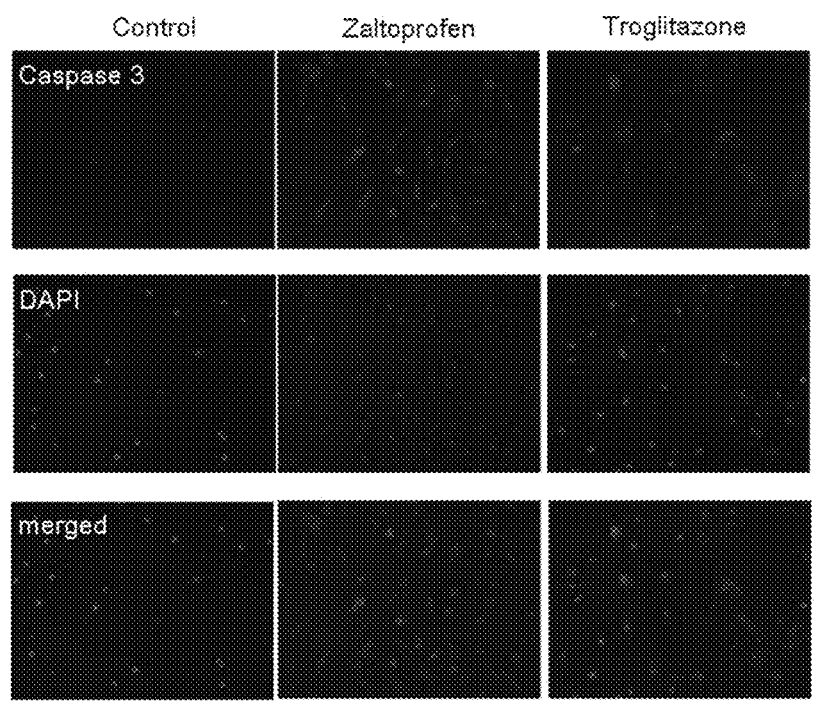
FIG. 24 Photographs showing results of caspase 3 staining of cultured cells derived from pigmented villonodular synovitis cultured in a zaltoprofen or troglitazone-containing medium.
Figure 25:
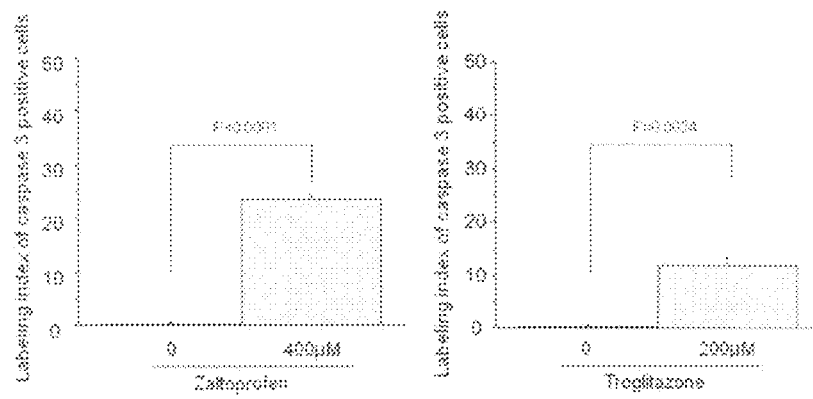
FIG. 25 Graphs showing ratios of caspase 3-positive cells in cultured cells derived from pigmented villonodular synovitis cultured in a zaltoprofen or troglitazone-containing medium.
Figure 26:
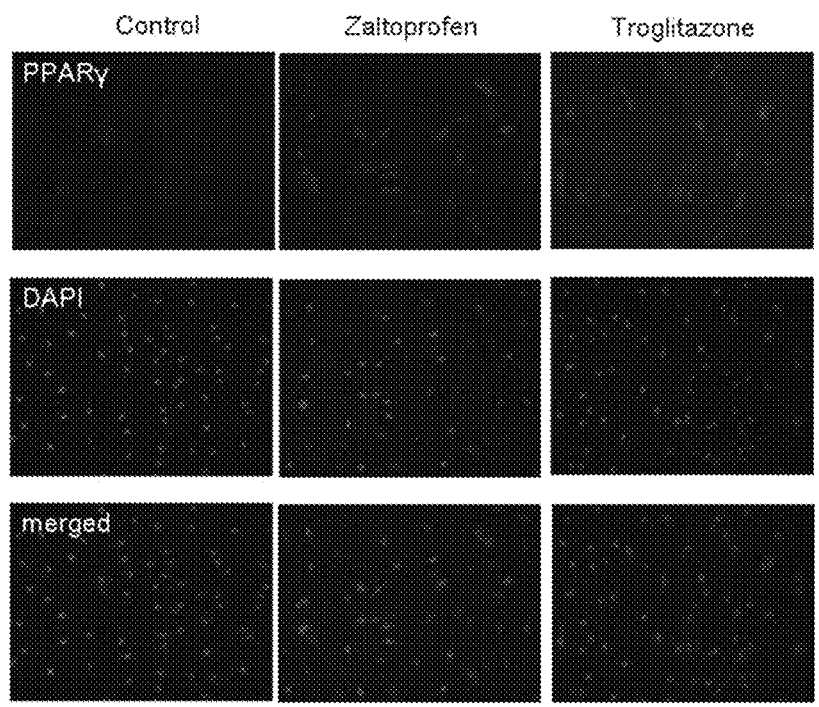
FIG. 26 Photographs showing results of PPARγ staining of cultured cells derived from giant cell tumor of tendon sheath cultured in a zaltoprofen or troglitazone-containing medium.
Figure 27:
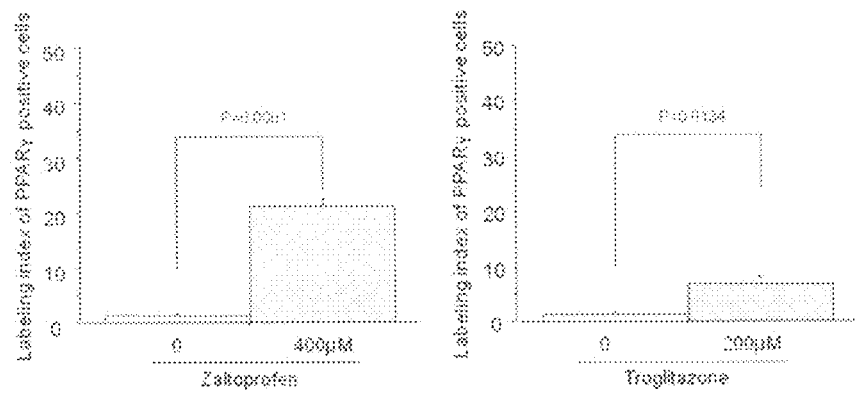
FIG. 27 Graphs showing ratios of PPARγ-positive cells in cultured cells derived from giant cell tumor of tendon sheath cultured in a zaltoprofen or troglitazone-containing medium.
Figure 28:
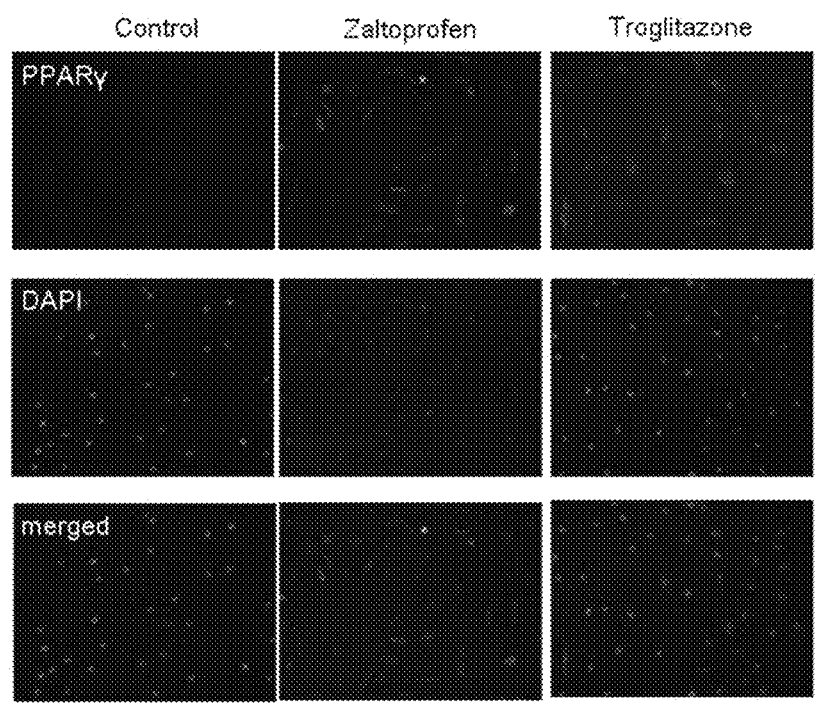
FIG. 28 Photographs showing results of PPARγ staining of cultured cells derived from pigmented villonodular synovitis cultured in a zaltoprofen or troglitazone-containing medium.
Figure 29:
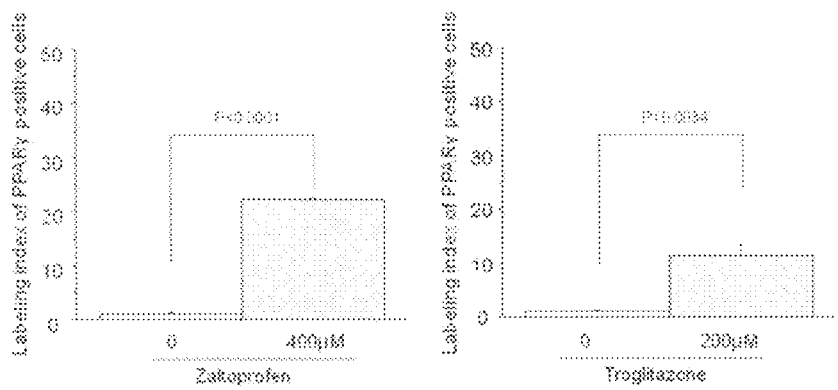
FIG. 29 Graphs showing ratios of PPARγ-positive cells in cultured cells derived from pigmented villonodular synovitis cultured in a zaltoprofen or troglitazone-containing medium.

Example 8: Analysis of Suppression of Cell Proliferation and Apoptosis of Cells Derived from Giant Cell Tumor of Tendon Sheath (GOT of Tendon Sheath) or Cells Derived from Pigmented Villonodular Synovitis (Diffuse-Type GOT) Observed after Addition of Non-Steroidal Anti-Inflammatory Agent or Thiazolidine Derivative Cultured cells of giant cell tumor of tendon sheath (patient with giant cell tumor of tendon sheath in the right knee, in 30's) and cultured cells of pigmented villonodular synovitis (patient with pigmented villonodular synovitis in the left knee, in 30's) were cultured in the same manner as that of Example 1, zaltoprofen or troglitazone was added to the cells at various concentrations, and absorbance was measured (FIGS. 16 and 17). As a result, it was observed that the cell proliferation was suppressed in a zaltoprofen or troglitazone concentration-dependent manner.

Further, in the same manner as that of Example 1, the cultured cells of giant cell tumor of tendon sheath and the cultured cells of pigmented villonodular synovitis were subjected to staining with caspase 3 and Tunel assay, and presence or absence of apoptosis was analyzed (FIGS. 18 to 25). As a result, it was observed that the Tunel-positive ratio and caspase 3-positive ratio increased in the cells added with zaltoprofen at a concentration of 400 μM or troglitazone at a concentration of 2000 μM compared with those observed for the control.

Example 9: PPARγ Immunostaining of Cells Derived from Giant Cell Tumor of Tendon Sheath (GCT of Tendon Sheath) or Cells Derived from Pigmented Villonodular Synovitis (Diffuse-Type GCT) Performed after Addition of Non-Steroidal Anti-Inflammatory Agent or Thiazolidine Derivative In the same manner as that of Example 2, zaltoprofen or troglitazone was added at concentration of 400 μM or 2000 μM, respectively, to the cells derived from giant cell tumor of tendon sheath or cells derived from pigmented villonodular synovitis, and PPARγ-positive images were observed (FIGS. 26 to 29). As a result, expression of PPARγ was successfully observed in the zaltoprofen or troglitazone-added cells.

Figure 30:
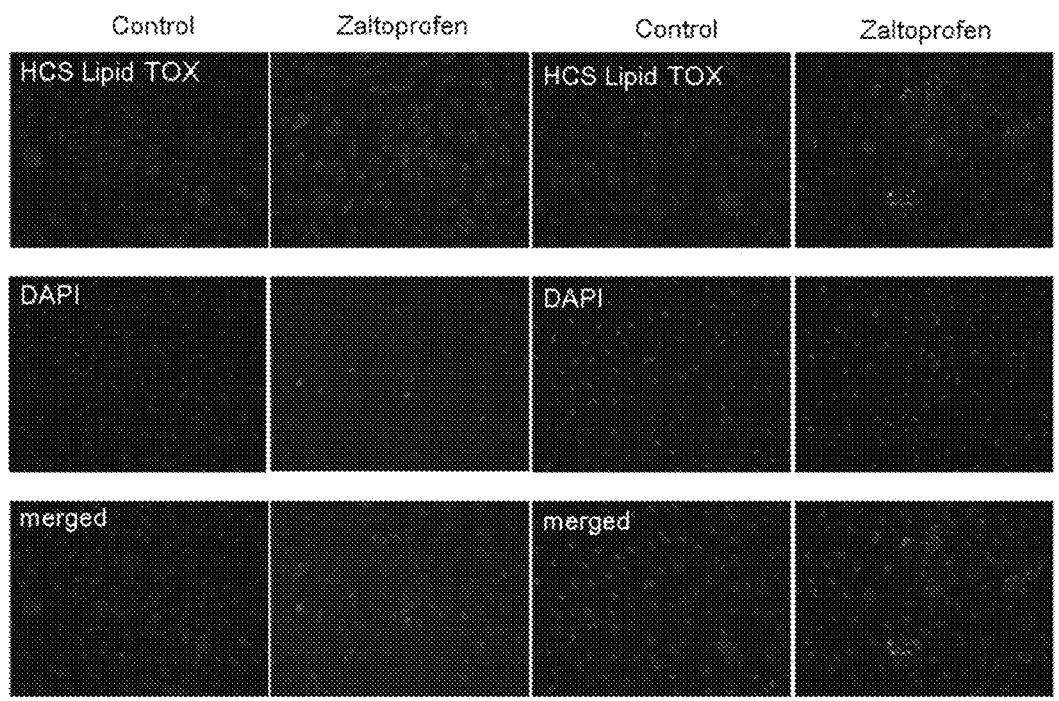
FIG. 30 Photographs showing results of lipid staining of cultured cells derived from giant cell tumor of tendon sheath or cultured cells derived from pigmented villonodular synovitis cultured in a zaltoprofen-containing medium.
Figure 31:
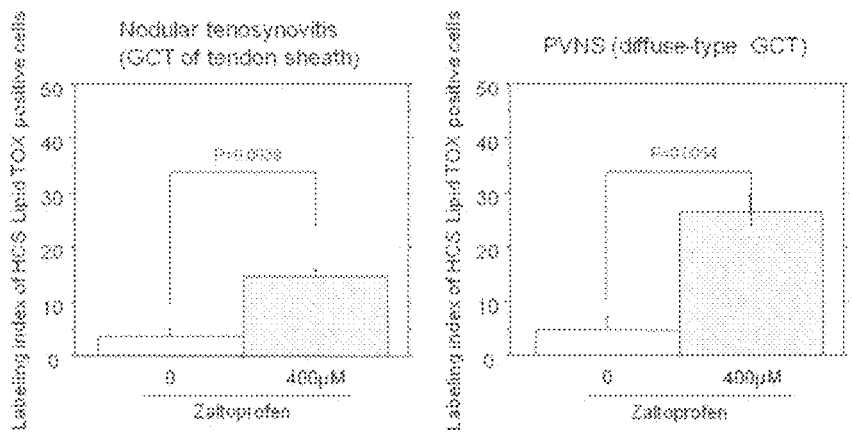
FIG. 31 Graphs showing ratios of lipid-positive cells in cultured cells derived from giant cell tumor of tendon sheath or cultured cells derived from pigmented villonodular synovitis cultured in a zaltoprofen-containing medium.

Example 10: Analysis of Fat Cell Differentiation of Cells Derived from Giant Cell Tumor of Tendon Sheath (GCT of Tendon Sheath) or Cells Derived from Pigmented Villonodular Synovitis (Diffuse-Type GCT) Observed after Addition of Non-Steroidal Anti-Inflammatory Agent As described in Example 3, it has been reported that PPARγ is a transcription factor indispensable for fat cell differentiation. Therefore, zaltoprofen was added at a concentration of 400 μM to the cells derived from giant cell tumor of tendon sheath or the cells derived from pigmented villonodular synovitis, and differentiation into fat cells was analyzed (FIGS. 30 and 31). As a result, it was successfully observed that the positive images obtained with HCS LipidTOX Green Neutral Lipid Stain increased in the zaltoprofen-added cells compared with the control.

Figure 32:
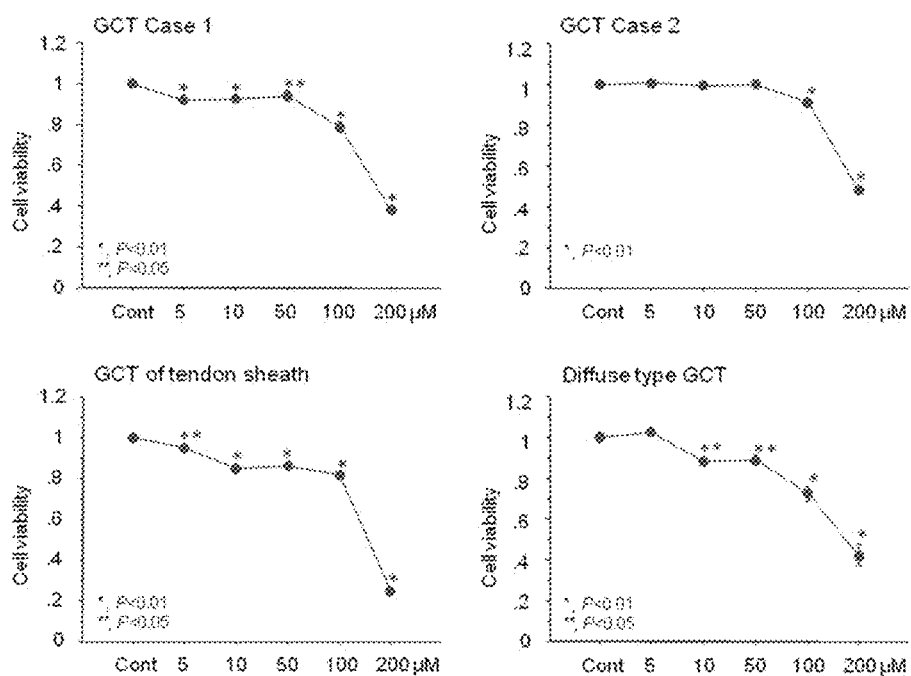
FIG. 32 Graphs showing results of suppression of proliferation of GCT cultured cells, cultured cells derived from giant cell tumor of tendon sheath, and cultured cells derived from pigmented villonodular synovitis cultured in a pioglitazone-containing medium.

Example 11: Analysis of Suppression of Cell Proliferation of Cultured Cells of Osteoclastoma (GCT) Observed after Addition of Pioglitazone In the same manner as that of Example 1, the GCT cultured cells (case 1, case 2), the cells derived from giant cell tumor of tendon sheath (GCT of tendon sheath), or the cells derived from pigmented villonodular synovitis (diffuse-type GCT) were cultured, and then pioglitazone, a thiazolidine derivative, was added at various concentrations, and absorbance was measured at 450 nm (FIG. 32). As a result, it was observed that the proliferation of cells was suppressed in a pioglitazone concentration-dependent manner.

Figure 33:
FIG. 33 A photograph showing an X-ray image of the pelvic part of a patient with recurrence of osteoclastoma in the pelvic part obtained before the administration of zaltoprofen.
Figure 34:
FIG. 34 A photograph showing an MRI image of the pelvic part of a patient with recurrence of osteoclastoma in the pelvic part obtained before the administration of zaltoprofen.
Figure 35:
FIG. 35 A photograph showing an MRI image of the pelvic part of a patient with recurrence of osteoclastoma in the pelvic part obtained after two months of the administration of zaltoprofen. The arrows indicate a tumor necrosis region.
Figure 36:
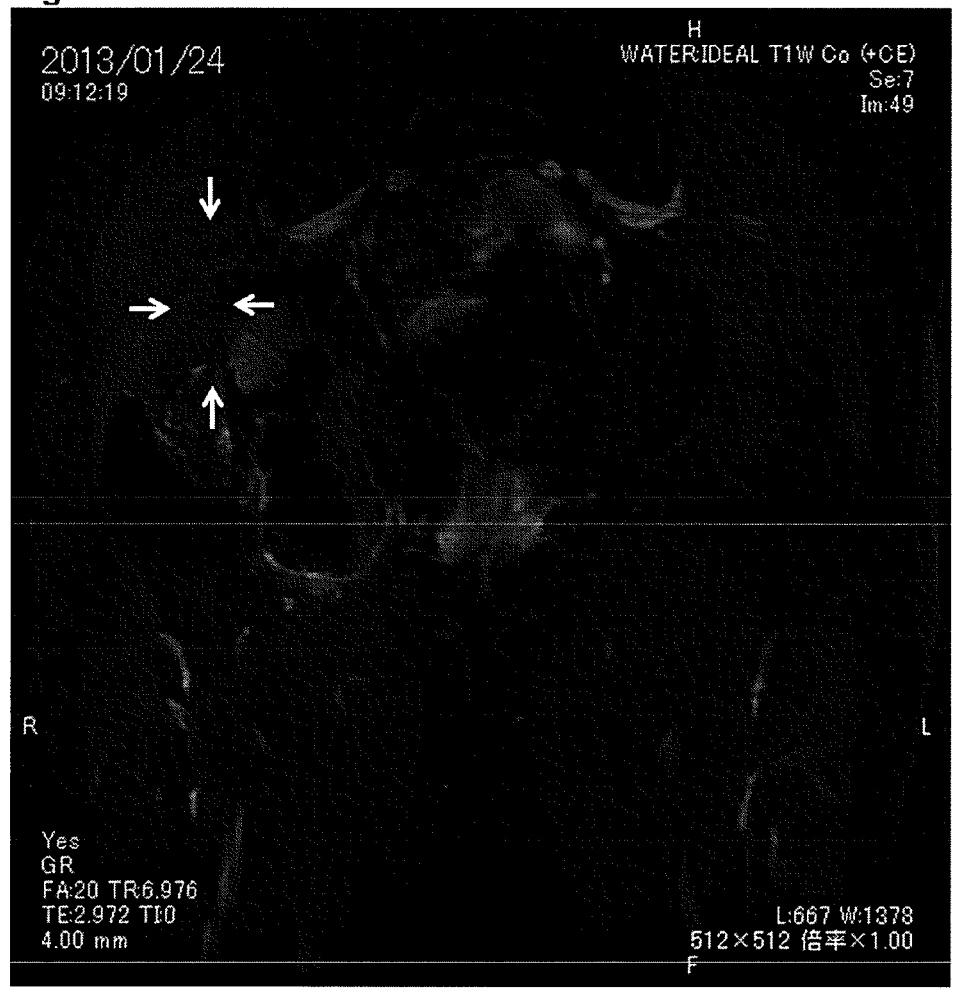
FIG. 36 A photograph showing an MRI image of the pelvic part of a patient with recurrence of osteoclastoma in the pelvic part obtained after four months of the administration of zaltoprofen. The arrows indicate a tumor necrosis region.
Figure 37:
FIG. 37 A photograph showing a sagittal MRI image of the right knee part of a patient with recurrence of pigmented villonodular synovitis in the right knee part obtained before the administration of zaltoprofen.
Figure 38:
FIG. 38 A photograph showing a transversal MRI image of the right knee part of a patient with recurrence of pigmented villonodular synovitis in the right knee part obtained before the administration of zaltoprofen.
Figure 39:
FIG. 39 A photograph showing a sagittal MRI image of the right knee part of a patient with recurrence of pigmented villonodular synovitis in the right knee part obtained after three months of the administration of zaltoprofen. The arrows indicate attenuation of the MRI imaging effect.
Figure 40:
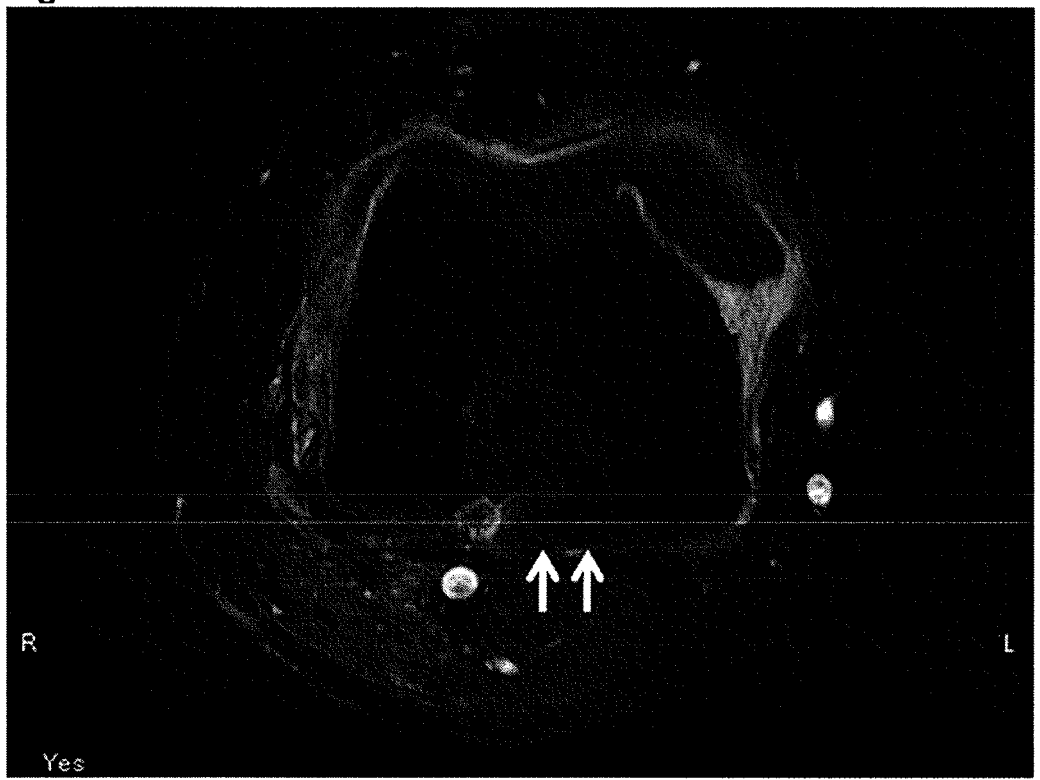
FIG. 40 A photograph showing a transversal MRI image of the right knee part of a patient with recurrence of pigmented villonodular synovitis in the right knee part obtained after three months of the administration of zaltoprofen. The arrows indicate attenuation of the MRI imaging effect.
Figure 41:
FIG. 41 A photograph showing a coronal MRI image of the right knee part of a patient with recurrence of pigmented villonodular synovitis in the right knee part obtained before the administration of zaltoprofen.
Figure 42:
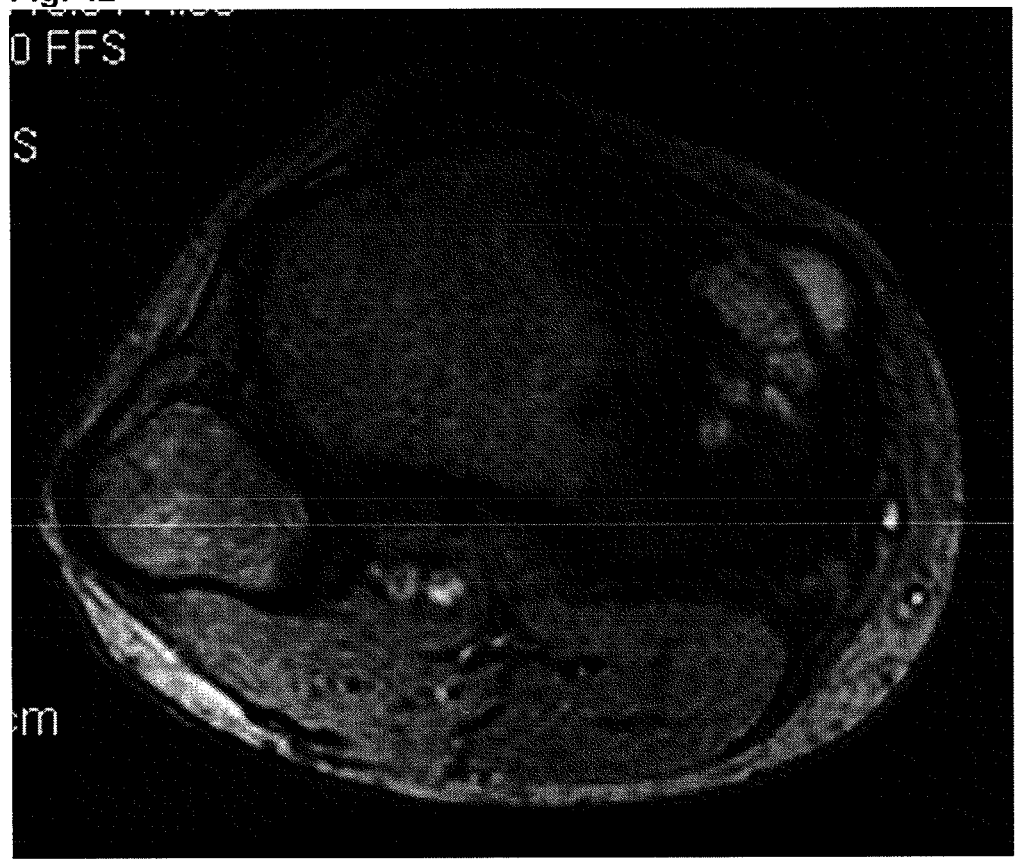
FIG. 42 A photograph showing a transversal MRI image of the right knee part of a patient with recurrence of pigmented villonodular synovitis in the right knee part obtained before the administration of zaltoprofen.
Figure 43:
FIG. 43 A photograph showing a coronal MRI image of the right knee part of a patient with recurrence of pigmented villonodular synovitis in the right knee part obtained after two months of the administration of zaltoprofen. The arrows indicate shrinkage of tumor.
Figure 44:
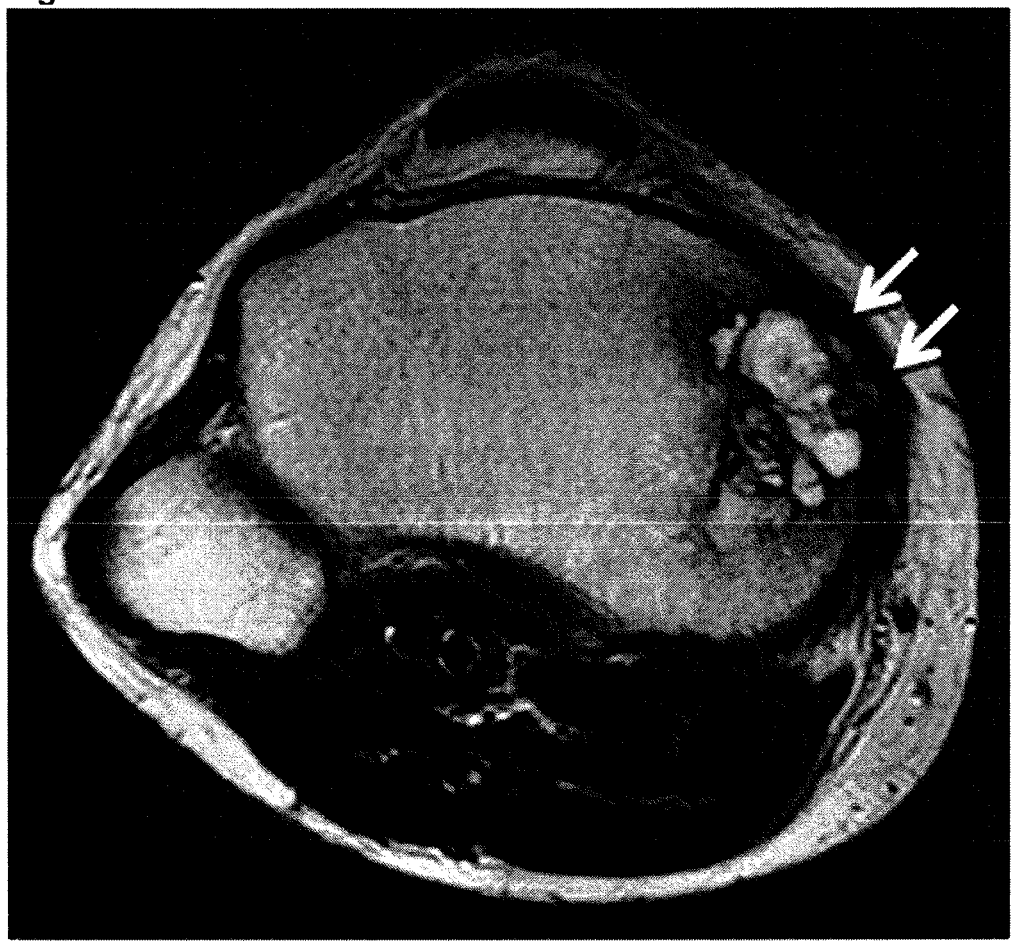
FIG. 44 A photograph showing a transversal MRI image of the right knee part of a patient with recurrence of pigmented villonodular synovitis in the right knee part obtained after two months of the administration of zaltoprofen. The arrows indicate shrinkage of tumor.

Example 12: Analysis of MRI Image of Patient with Osteoclastoma (GCT), Patient with Giant Cell Tumor of Tendon Sheath, or Patient with Pigmented Villonodular Synovitis Administered with Zaltoprofen Soleton Tablet 80 (generic name: zaltoprofen, 80 mg, Nippon Chemiphar) was administered to a patient with osteoclastoma, a patient with giant cell tumor of tendon sheath, or a patient with pigmented villonodular synovitis at a dose of 3 tablets per day (administered in morning, at noon, and in evening), and the tumor size was evaluated by MRI every several months. As a typical case, in a case of recurrence of osteoclastoma in the pelvic part (34 years old, female, FIGS. 33 and 34), gradual shrinkage of the tumor was observed after two months (FIG. 35) and four months (FIG. 36). Further, in a case of recurrence of pigmented villonodular synovitis in the right knee (26 years old, female, FIGS. 37 and 38), attenuation of MRI imaging effect was successfully observed after three months (FIGS. 39 and 40), and improvement was observed for pain and knee-joint excursion. Furthermore, in another case of recurrence of pigmented villonodular synovitis in the right knee (38 years old, female, FIGS. 41 and 42), shrinkage of tumor and improvement of pain was successfully observed after two months (FIGS. 43 and 44).

Figure 45:
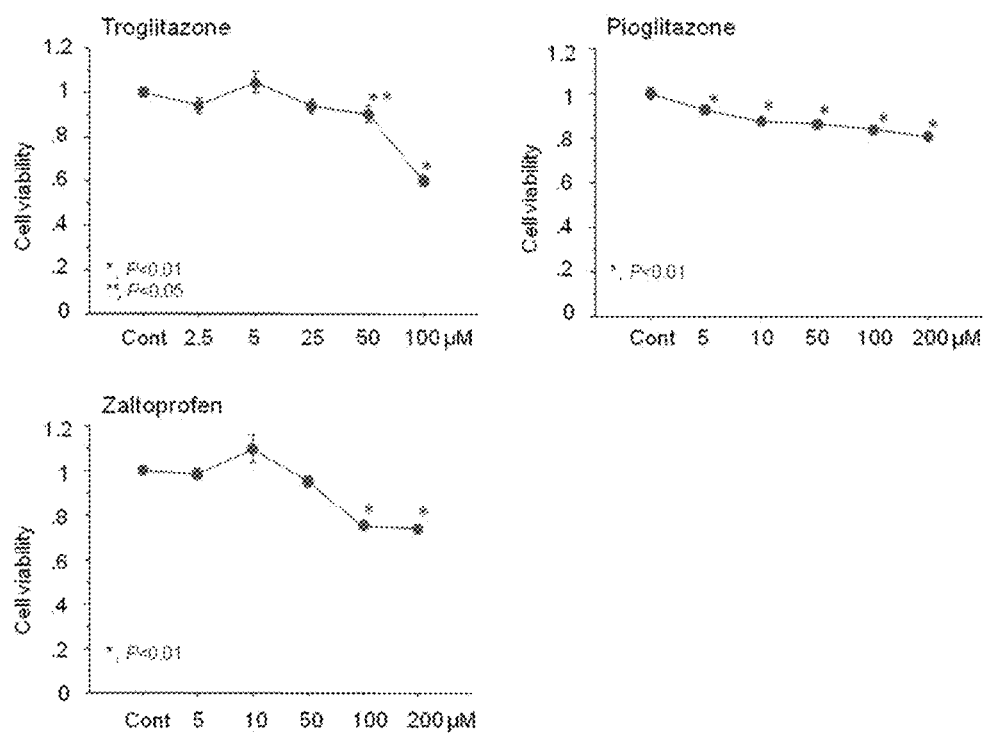
FIG. 45 Graphs showing results of suppression of proliferation of a chondrosarcoma-derived cell line cultured in a zaltoprofen, troglitazone, or pioglitazone-containing medium.

Example 13: Analysis of Suppression of Cell Proliferation and Apoptosis of Chondrosarcoma-Derived Cell Line (H-EMC-SS) Observed after Addition of Non-Steroidal Anti-Inflammatory Agent or Thiazolidine Derivative In the same manner as that of Example 1, the cell line derived from chondrosarcoma was cultured, troglitazone, pioglitazone, or zaltoprofen was added at various concentrations, and absorbance was measured (FIG. 45). As a result, it was observed that the cell proliferation was suppressed in a troglitazone, pioglitazone, or zaltoprofen concentration-dependent manner.

Figure 46:
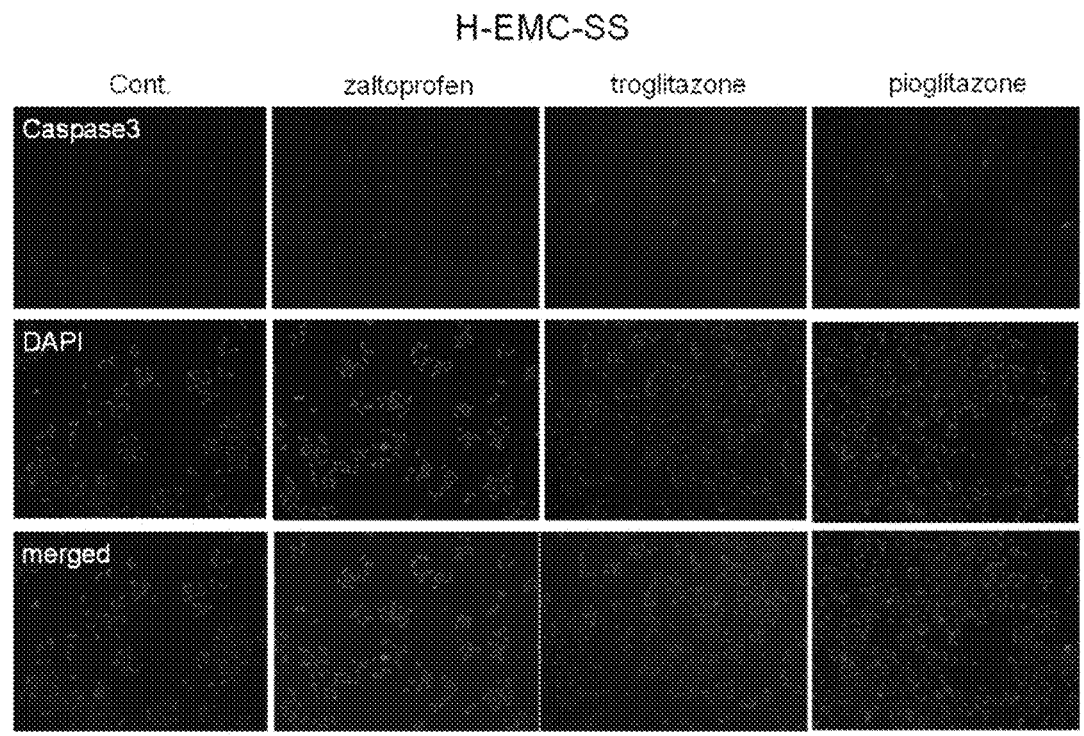
FIG. 46 Photographs showing results of caspase 3 staining of a chondrosarcoma-derived cell line cultured in a zaltoprofen, troglitazone, or pioglitazone-containing medium.
Figure 47:
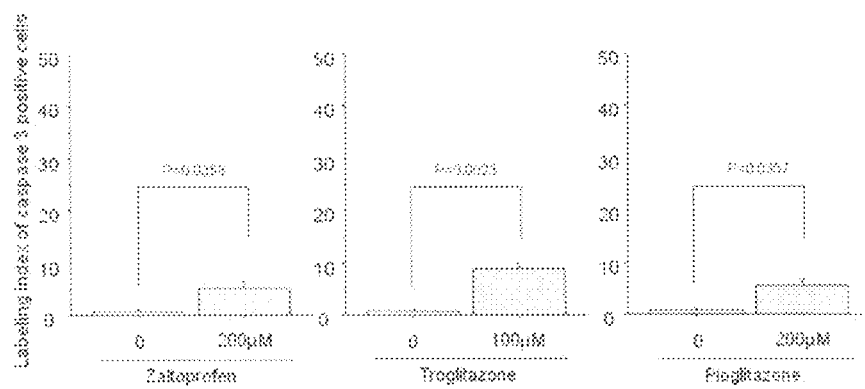
FIG. 47 Graphs showing ratios of caspase 3-positive cells in cells of a chondrosarcoma-derived cell line cultured in a zaltoprofen, troglitazone, or pioglitazone-containing medium.

Further, in the same manner as that of Example 1, the chondrosarcoma-derived cell line was subjected to caspase 3 staining, and presence or absence of apoptosis was analyzed (FIGS. 46 and 47). As a result, it was successfully observed that the caspase 3-positive ratio increased in the cells added with zaltoprofen at a concentration of 200 µM, troglitazone at a concentration of 100 µM, or pioglitazone at a concentration of 200 µM, compared with the control.

Figure 48:
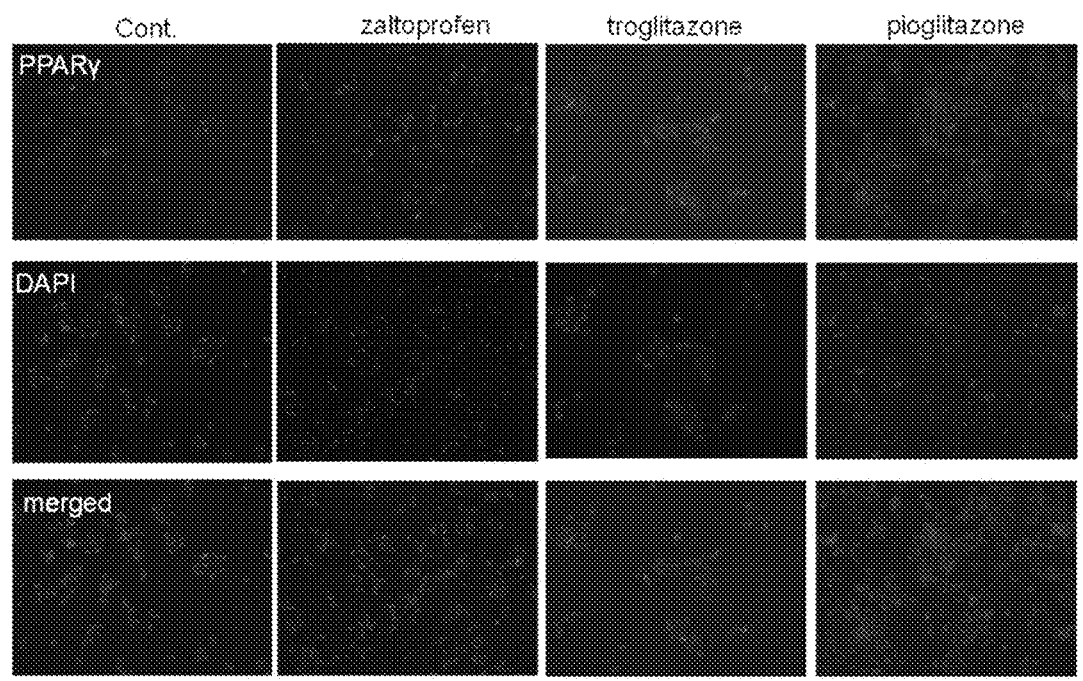
FIG. 48 Photographs showing results of PPARγ staining of a chondrosarcoma-derived cell line cultured in a zaltoprofen, troglitazone, or pioglitazone-containing medium.
Figure 49:
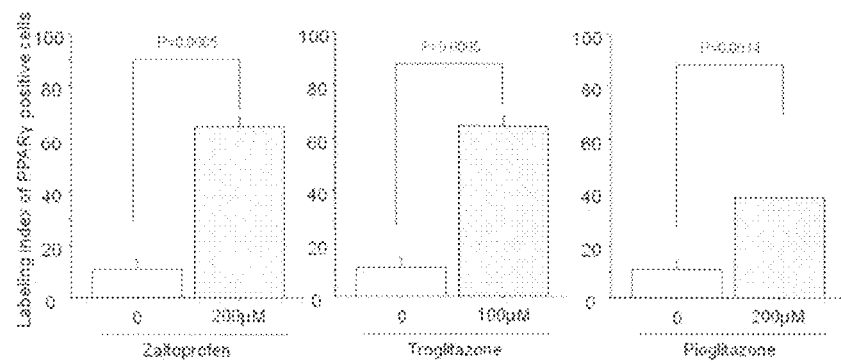
FIG. 49 Graphs showing ratios of PPARγ-positive cells in cells of a chondrosarcoma-derived cell line cultured in a zaltoprofen, troglitazone, or pioglitazone-containing medium.

Example 14: PPARγ Immunostaining of Chondrosarcoma-Derived Cell Line (H-EMC-SS) Performed after Addition of Non-Steroidal Anti-Inflammatory Agent or Thiazolidine Derivative In the same manner as that of Example 2, to the chondrosarcoma-derived cell line was added zaltoprofen at a concentration of 200 µM, troglitazone at a concentration of 100 µM, or pioglitazone at a concentration of 200 and the PPARγ-positive images were measured (FIGS. 48 and 49). As a result, expression of PPARγ was successfully observed in the zaltoprofen, troglitazone, or pioglitazone-added cells.

INDUSTRIAL APPLICABILITY

The prophylactic or therapeutic agent of the present invention is effective for a patient with giant cell tumor occurring in a bone and soft tissue or with chondrosarcoma, or a person having a risk of onset of giant cell tumor occurring in a bone and soft tissue or that of chondrosarcoma. Further, according to the present invention, research of a novel therapeutic agent for giant cell tumors occurring in a bone and soft tissue or chondrosarcoma is achievable by selecting a test substance that controls the PPARγ gene and apoptosis, or fat cell differentiation.

This application claims Conventional priorities based on Japanese Patent Application Nos. 2012-070351 (filing date: Mar. 26, 2012) and 2012-235784 (filing date: Oct. 25, 2012) filed at the Japanese Patent Office, and all the disclosures thereof are incorporated into the disclosure of this application.

What is claimed is:

1. A method for therapeutic treatment of osteoclastoma, giant cell tumor of tendon sheath, pigmented villonodular synovitis or chondrosarcoma, which comprises administering a therapeutically effective amount of zaltoprofen to a subject in need thereof, and wherein the therapeutically effective amount comprises the zaltoprofen as a single active pharmaceutical ingredient.

2. The method for therapeutic treatment according to claim 1, wherein the zaltoprofen is administered in an amount of 240 mg per day.

3. The method for therapeutic treatment according to claim 1, wherein the zaltoprofen is administered daily for at least 28 consecutive days.

4. The method according to claim 1, wherein the tumor size of said osteoclastoma, giant cell tumor of tendon sheath, pigmented villonodular synovitis or chondrosarcoma is decreased.

5. The method according to claim 1, wherein the proliferation of said osteoclastoma, giant cell tumor of tendon sheath, pigmented villonodular synovitis or chondrosarcoma is suppressed.

6. The method according to claim 4, wherein the zaltoprofen is administered in an amount of 240 mg per day.

7. The method according to claim 4, wherein the zaltoprofen is administered daily for at least 28 consecutive days.

8. The method according to claim 5, wherein the zaltoprofen is administered in an amount of 240 mg per day.

9. The method according to claim 5, wherein the zaltoprofen is administered daily for at least 28 consecutive days.

* * * * *